(12) United States Patent
Antharavally et al.

(10) Patent No.: US 11,813,550 B2
(45) Date of Patent: *Nov. 14, 2023

(54) METHOD FOR PRODUCING PURIFIED STEVIOL PRODUCT USING SIMULATED MOVING BED CHROMATOGRAPHY

(71) Applicant: Orochem Technologies Inc., Naperville, IL (US)

(72) Inventors: Babu Siddegowda Antharavally, Caledonia, IL (US); Anil R. Oroskar, Oak Brook, IL (US); Asha A. Oroskar, Oak Brook, IL (US)

(73) Assignee: Orochem Technologies Inc., Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/410,735

(22) Filed: Aug. 24, 2021

(65) Prior Publication Data
US 2021/0379508 A1     Dec. 9, 2021

Related U.S. Application Data

(63) Continuation of application No. 16/600,159, filed on Oct. 11, 2019, now Pat. No. 11,097,206, which is a (Continued)

(51) Int. Cl.
*A23L 5/20* (2016.01)
*B01D 15/18* (2006.01)
(Continued)

(52) U.S. Cl.
CPC .............. *B01D 15/185* (2013.01); *A23L 5/23* (2016.08); *A23L 27/33* (2016.08);
(Continued)

(58) Field of Classification Search
CPC .......... A23L 5/23; A23L 27/33; B01D 61/58; B01D 2311/2626; B01D 15/185
See application file for complete search history.

(56) References Cited

U.S. PATENT DOCUMENTS

| 2,985,589 A | 5/1961 | Broughton |
| 6,228,996 B1 | 5/2001 | Zhou et al. |

(Continued)

FOREIGN PATENT DOCUMENTS

| JP | 2011-051909 A | 3/2011 |
| WO | WO 2009/140394 A1 | 11/2009 |

(Continued)

OTHER PUBLICATIONS

Anonymous, "Steviol Glycosides," FAO JECFA Monographs 4 (2007).
(Continued)

*Primary Examiner* — Bradley R Spies
(74) *Attorney, Agent, or Firm* — Leydig, Voit & Mayer, Ltd.

(57) ABSTRACT

Disclosed is a continuous process for the purification of steviol glycosides such as Rebaudioside D and/or Rebaudioside M extracted from the dried stevia leaves or extracted from a fermentation broth using continuous simulated moving bed processes and nanofiltration without the addition of organic solvents to obtain a purified steviol product comprising sweet steviol glycosides. The sweet steviol glycosides can be used as substitutes for caloric sweeteners in beverages and in other food items.

24 Claims, 13 Drawing Sheets

Related U.S. Application Data continuation-in-part of application No. 16/256,868, filed on Jan. 24, 2019, now Pat. No. 10,898,829, which is a continuation of application No. 15/375,040, filed on Dec. 9, 2016, now Pat. No. 10,213,707.

(51) Int. Cl.

| | | |
|---|---|---|
| *B01D 15/32* | (2006.01) | |
| *B01D 15/36* | (2006.01) | |
| *B01D 61/04* | (2006.01) | |
| *B01D 61/58* | (2006.01) | |
| *C07H 1/08* | (2006.01) | |
| *C07H 15/24* | (2006.01) | |
| *A23L 27/30* | (2016.01) | |
| *B01D 61/02* | (2006.01) | |
| *B01D 61/14* | (2006.01) | |

(52) U.S. Cl.
CPC ....... *B01D 15/1842* (2013.01); *B01D 15/327* (2013.01); *B01D 15/362* (2013.01); *B01D 15/363* (2013.01); *B01D 61/026* (2022.08); *B01D 61/027* (2013.01); *B01D 61/04* (2013.01); *B01D 61/147* (2013.01); *B01D 61/58* (2013.01); *C07H 1/08* (2013.01); *C07H 15/24* (2013.01); *A23V 2002/00* (2013.01); *B01D 2311/04* (2013.01); *B01D 2311/08* (2013.01); *B01D 2311/2626* (2013.01); *B01D 2317/022* (2013.01)

(56) References Cited

U.S. PATENT DOCUMENTS

| | | |
|---|---|---|
| 6,476,239 B1 | 11/2002 | Arumugam |
| 7,423,026 B2 | 9/2008 | Järvinen et al. |
| 7,592,026 B2 | 9/2009 | Hartmann et al. |
| 7,592,328 B2 | 9/2009 | Jarho et al. |
| 8,158,134 B1 | 4/2012 | Supersaxo et al. |
| 9,169,285 B2 | 10/2015 | Prakash et al. |
| 2011/0087011 A1 | 4/2011 | Chiang et al. |
| 2013/0274351 A1 | 10/2013 | Markosyan et al. |
| 2014/0099403 A1 | 4/2014 | Prakash et al. |
| 2015/0017284 A1 | 1/2015 | Prakash et al. |
| 2018/0161696 A1 | 6/2018 | Oroskar et al. |

FOREIGN PATENT DOCUMENTS

| | | |
|---|---|---|
| WO | WO 2017/183011 A1 | 10/2017 |
| WO | WO 2019/189422 A1 | 10/2019 |

OTHER PUBLICATIONS

"Background review for cyclodextrins used as excipients" *European Medicines Agency*, 17 pages (Nov. 20, 2014).

Jahro et al., "Hydroxypropyl-β-Cyclodextrin and Its Combination With Hydroxypropyl-Methylcellulose Increase Aqueous Solubility of-$\Delta^9$-Tetrahydrocannabinol," *Life Sciences*, 63(26):, PL 381-384 (1998).

Malanga et al., ""Back to the Future": A New Look at Hydroxypropyl Beta-Cyclodextrins," *Journal of Pharmaceutical Sciences*, 105: 2921-2931 (2016).

Mannila et al., "Effects of RM- β-CD on sublingual bioavailability of $\Delta^9$-tetrahydrocannabinol in rabbits," *European Journal of Pharmaceutical Sciences* 26: 71-77 (2005).

Mannila et al., "Precipitation Complexation Method Produces Cannabidiol/β -Cyclodextrin Inclusion Complex Suitable for Sublingual Administration of Cannabidiol," *Journal of Pharmaceutical Sciences*, 96(2): 312-319 (2007).

Prakash et al., "Development of Next Generation Stevia Sweetener: Rebaudioside M", Foods, 3: 162-175, MDPI AG, Basel, Switzerland (2014).

European Patent Office, International Search Report and the Written Opinion in International Application No. PCT/US2019/041865 (dated Oct. 24, 2019).

European Patent Office, International Search Report and the Written Opinion in International Application No. PCT/US2020/055168 (dated Feb. 3, 2021).

METHOD FOR PRODUCING PURIFIED STEVIOL PRODUCT USING SIMULATED MOVING BED CHROMATOGRAPHY

CROSS-REFERENCE TO RELATED APPLICATIONS

This patent application is a continuation of U.S. patent application Ser. No. 16/600,159, filed Oct. 11, 2019, which is a continuation-in-part of U.S. patent application Ser. No. 16/256,868, filed Jan. 24, 2019, which is a continuation of U.S. patent application Ser. No. 15/375,040, filed on Dec. 9, 2016, and entitled, "Continuous Process for Purification of Steviol Glycosides from Stevia Leaves Using Simulated Moving Bed Chromatography," each of which are incorporated in their entireties herein by this reference.

FIELD OF THE INVENTION

The invention relates to a method for purification and separation of steviol glycosides (e.g., Rebaudioside D and/or Rebaudioside M) from dried stevia leaves and continuous purification of steviol glycosides. More particularly, the method relates to a process for the continuous purification of steviol glycosides (e.g., Rebaudioside D and/or Rebaudioside M) extracted from the dried stevia leaves using simulated moving bed chromatography. Most particularly, the method relates to a novel continuous process for the purification of steviol glycosides (e.g., Rebaudioside D and/or Rebaudioside M) extracted from the dried stevia leaves using a continuous simulated moving bed process using water exclusively as the mobile phase desorbent without the addition of organic solvents to obtain a purified steviol product comprising sweet steviol glycosides. The sweet steviol glycosides can be used as substitutes for caloric sweeteners in beverages and in other food items.

BACKGROUND

The worldwide demand for high potency sweeteners is increasing and, with blending of different sweeteners becoming a standard practice, the demand for alternatives is expected to increase. Such sweeteners include both caloric and low-caloric sweeteners. Caloric sweeteners include sucrose, fructose, and glucose. Recently, low-calorie (or non-calorie) sweeteners have gained increased popularity. These can be used as substitutes for caloric sweeteners and are often referred to as "sugar substitutes". Common sugar substitutes include saccharin, aspartame, and sucralose.

One such low-calorie sweetener is stevia, which is a sweetener derived from Steviol glycosides. Demand for Steviol glycosides is growing because of their non-toxic nature, their sugar-like taste profile, and their low caloric value, when used as sugar substitutes.

*Stevia rebaudiana* Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10 to 20% of the total dry weight. These diterpene glycosides are about 150 to 450 times sweeter than sugar. Structurally, the diterpene glycosides are characterized by a single base, steviol, and differ by the presence of carbohydrate residues at positions C13($R_2$) and C19($R_1$). The structure of the steviol base is shown hereinbelow:

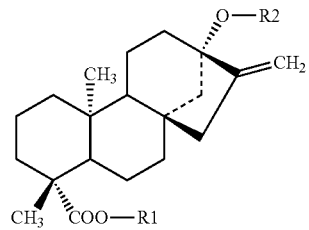

Table 1 illustrates the various steviol compounds with reference to the above steviol base.

TABLE 1

Chemical Structures of Steviol Glycosides

R-Groups in Stevia Structure

| Compound | $R_1$ | $R_2$ | Formula | MW |
|---|---|---|---|---|
| Rebaudioside A | β-glc- | (β-glc)$_2$-β-glc- | $C_{44}H_{70}O_{23}$ | 967.01 |
| Rebaudioside B | H | (β-glc)$_2$-β-glc- | $C_{38}H_{60}O_{18}$ | 804.88 |
| Rebaudioside C | β-glc- | (β-glc, α-rha-)-β-glc | $C_{44}H_{70}O_{22}$ | 951.01 |
| Rebaudioside D | β-glc-β-glc- | (β-glc)$_2$-β-glc- | $C_{50}H_{80}O_{28}$ | 1129.15 |
| Rebaudioside E | β-glc-β-glc- | β-glc-β-glc- | $C_{44}H_{70}O_{23}$ | 967.01 |
| Rebaudioside F | β-glc- | (β-glc, β-xyl)-β-glc- | $C_{43}H_{68}O_{22}$ | 936.99 |
| Rebaudioside M | (β-glc)$_2$-β-glc- | (β-glc)$_2$-β-glc | $C_{56}H_{90}O_{33}$ | 1291.3 |
| Stevioside | β-glc- | β-glc-β-glc- | $C_{38}H_{60}O_{18}$ | 804.88 |
| Steviolbioside | H | β-glc-β-glc- | $C_{32}H_{50}O_{13}$ | 642.73 |
| Rubusoside | β-glc- | β-glc- | $C_{32}H_{50}O_{13}$ | 642.73 |
| Dulcoside A | β-glc- | α-rha-β-glc- | $C_{38}H_{60}O_{17}$ | 788.87 |

Glc—glucose;
rha—rhamnose;
xyl—xylose

Typically, on a dry weight or anhydrous basis, the four major steviol glycosides found in the leaves of stevia are Dulcoside A (0.3%), Rebaudioside C (0.6-1.0%), Rebaudioside A (3.8%) and Stevioside (9.1%). Other glycosides identified in Stevia extract include one or more of Rebaudioside B, D, E, F, G, H, I, J, K, L, M, N, and O, Steviolbioside, Rubusoside and are present in very low concentrations in stevia leaves.

Among these, only Stevioside and Rebaudioside A are available on a commercial scale. Stevioside and Rebaudioside A are the component glycosides of principal interest for their sweetening property. However, Rebaudioside A can suffer from off-taste issues. Potential alternatives include Rebaudioside D and Rebaudioside M, which have higher sweetness intensity and are more potent than other steviol glycosides. For example, Rebaudioside D and Rebaudioside M are about 200-250 times sweeter than sucrose, but have a less sweet lingering aftertaste and bitterness compared to Rebaudioside A. However, due to the low abundance of Rebaudioside D and Rebaudioside M relative to Rebaudioside A, isolation and purification can be costly and ineffective.

Steviol glycosides can be extracted from leaves using either water or organic solvent extraction. Typically, steviol glycosides are obtained from the leaves of *Stevia rebaudiana* Bertoni. The leaves are extracted with hot water and the resulting aqueous extract is passed through an adsorption resin to trap and concentrate the component steviol glycosides. Generally, the resin is desorbed by washing the resin with organic solvents like methanol or ethanol to release the glycosides. Typically, the steviol product is recrystallized with a solvent such as methanol or ethanol. Typically, the steviol product is recrystallized with a solvent such as methanol. Ion-exchange resins have been used in the purification process. The final product is typically spray-dried. (See *FAO JECFA Monographs* 4 (2007).

Supercritical fluid extraction and steam distillation methods have also been described. Methods for the recovery of diterpene sweet glycosides from *Stevia rebaudiana Bertoni* using supercritical $CO_2$, membrane technology, and water or organic solvents, such as methanol and ethanol, may also be used.

Because the chemical structures of the steviol glycosides are very similar, obtaining a relatively pure form of a single rebaudioside from the mixture of other isomers is a challenge. Conventional methods for purification of rebaudiosides typically require a cascade of process steps including: filtration, precipitation of undesired components, decolorization, anion and cation exchange, and multi-stage crystallization to provide a purity of 95 weight percent on a dry or anhydrous basis. Often these steps include at least four solvent changes, drying and resolving steps.

U.S. Pat. No. 6,228,996 discloses a method for purifying diterpene glycosides from plant sources wherein the plant components such as fruit, leaves, branches, and bark, etc., are extracted to obtain a liquid extract. The liquid extract is admixed with a saturated solution containing at least one metallic ion having a valence of 2 or 3 (preferably, Al+++), and the resulting admixture is contacted with a resin to adsorb the diterpene glycosides of interest. The diterpene glycosides are desorbed from the resin by washing the resin with an alcohol solution to obtain an alcohol solution containing the diterpene glycosides. The alcohol solution is subsequently dried to provide a dry composition containing the diterpene glycosides.

U.S. Pat. No. 9,169,285 discloses methods for purifying steviol glycosides which include (a) passing a solution of steviol glycosides through a multi-column system including a plurality of columns packed with an adsorbent resin to provide at least one column having adsorbed steviol glycosides; (b) eluting the adsorbed fractions from the at least one column having adsorbed steviol glycosides using a desorbent being a solution comprising alcohol and water to provide an eluted alcoholic solution with high steviol glycoside content. Further processing steps include ion-exchange and decolorizing the eluted solution before solvent removal and drying steps to obtain a solid steviol glycoside product.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

Conventional methods for the purification of Steviol glycoside extracts are associated almost exclusively with the use of organic solvents, such as methanol, ethanol or ether. Typically, such methods require that the Steviol glycosides be initially absorbed on a resin, followed by elution of the adsorbed Steviol glycosides with an organic solvent. Thus concentrated, the resulting organic Steviol glycoside solutions are evaporated and further treated with an alcohol such as methanol or ethanol in a crystallization step to provide a purified, crystallized steviol glycoside product. To satisfy the growing demand for the stevia based sweeteners which meet commercial food quality requirements, there is a need for an efficient extraction process that can be carried out to produce the main sweetening components without the use of organic solvents. More particularly, there is a need for an affordable process capable of isolating limited Steviol glycosides such as Rebaudioside D and Rebaudioside M, which meets commercial food quality requirements. The potential for even small amounts of organic solvents remaining in the purified stevia glycoside product can be deleterious to human health.

SUMMARY

The process of the present invention relates to the purification of steviol glycosides (e.g., Rebaudioside D and/or Rebaudioside M) directly from extracts of plant material in a process which uses novel chromatographic scheme. More specifically, Applicant has developed a sequence of purification steps and a novel simulated moving bed separation process (SMB) series of adsorbent/desorbent combinations and SMB configurations to bring about the enrichment and purification of steviol glycosides (e.g., Rebaudioside D and/or Rebaudioside M) from extracts of the stevia plant such as, *Stevia rebaudiana Bertoni*, to provide a purified steviol glycoside product and without using any potentially toxic organic solvent. The simulated moving bed system employed uses a combination of cationic, anionic, and hydrophobic interaction stationary phase adsorbents and a mobile phase comprising water in a combination of normal and reverse phase simulated moving bed separation zones to provide an enriched extract stream comprising major steviol glycosides (e.g., Rebaudioside D and/or Rebaudioside M). A steviol glycoside product having a total steviol glycoside (TSG) purity greater than 95 wt. percent (e.g., 96, 97, 98, 99, 99.5 wt. %) following evaporation or drying can be obtained.

In some embodiments, the invention relates to a continuous process for the purification of steviol glycosides from a crude steviol glycoside extract to provide a purified steviol glycoside product. The crude steviol glycoside extract comprises Rebaudioside D and/or Rebaudioside M, other steviol glycosides, water, tri-terpenes, sterols, flavonoids, volatile oils, pigments, gums, proteins, carotenoids, chlorophyll, vitamins, phospholipids, saccharides, solid insolubles and salts. The process comprises:

a) passing the crude steviol glycoside extract to a first filtration zone comprising a microfiltration filter having a pore size of less than about 0.2 μm to remove at least a portion of the solid insolubles to provide a filtered steviol glycoside extract;

b) passing the filtered steviol glycoside extract and a first mobile phase desorbent stream consisting of water to a first swing bed simulated moving bed zone comprising a plurality of first swing adsorbent beds containing a hydrophobic interaction resin selective adsorbent to adsorb Rebaudioside D and/or Rebaudioside M, and other steviol glycosides to provide a first swing bed extract stream comprising Rebaudioside D and/or Rebaudioside M, water, and other steviol glycosides and a first group of impurities including proteins, vitamins, phospholipids, saccharides, and salts, and to provide a primary first swing bed raffinate stream comprising Rebaudioside D and/or Rebaudioside M, water, and other steviol glycosides and a secondary first swing bed raffinate comprising water, tri-terpenes, sterols, flavonoids, carotenoids chlorophyll, volatile oils, pigments, and gums and combining at least a portion of the primary first swing bed raffinate with the first swing bed extract stream wherein the hydrophobic interaction resin selective adsorbent comprises an aromatic non-polar copolymer of styrene-divinyl benzene resin;

c) passing the first swing bed extract stream to a first nanofiltration zone to remove at least a portion of water from the first swing bed extract stream to provide a first nano retentate stream and a first nano permeate stream comprising water;

d) passing the first nano retentate stream and a second mobile phase desorbent comprising water to a second swing bed simulated moving bed zone comprising a plurality of second swing adsorbent beds which are disposed in pairs wherein a first second swing adsorbent bed in each pair contains a strongly acidic cationic resin and a second swing adsorbent bed in each pair contains a weakly basic anionic resin, said plurality of second swing adsorbent beds in the second swing bed simulated moving bed zone being divided into an adsorption/desorption zone wherein each pair of second swing adsorbent beds is disposed in serial fluid communication and a regeneration zone wherein a first pair of second swing adsorbent beds is in serial communication and a second pair of second swing adsorbent beds comprise a regeneration zone cation bed and a regeneration zone anion bed, wherein the first nano retentate stream and a second mobile phase desorbent are intermittently passed to the adsorption/desorption zone to adsorb salts, pigment and proteins from the first nano retentate stream to provide a second swing bed elute stream comprising steviol glycosides, water, phospholipids, and saccharides, and on desorption with the second mobile phase desorbent provide a second swing bed raffinate stream comprising water, proteins, pigments and salts, and the regeneration zone comprises simultaneously passing a second swing bed water wash stream to the first pair of second swing adsorbent beds in the regeneration zone and simultaneously and sequentially passing a basic wash stream, the second swing bed water wash stream, an acid wash stream, and the second swing bed water wash stream to condition the regeneration zone cation bed, and simultaneously and sequentially passing the basic wash stream and the second swing bed water wash stream to condition the regeneration zone anion bed to regenerate the regeneration zone and provide a second swing bed waste water stream which is admixed with the second swing bed raffinate stream;

e) passing the second swing bed elute stream and a third mobile phase desorbent stream comprising water to a polishing bed simulated moving bed zone, said polishing bed simulated moving bed zone comprising a plurality of polishing bed adsorbent beds containing a hydrophobic interaction resin selective for first eluting a polishing zone total raffinate stream comprising saccharides and phospholipids, and to provide a polishing bed extract stream comprising steviol glycosides, said polishing bed extract stream comprising water and an enhanced amount of steviol glycosides relative to the amount of steviol glycosides in the crude steviol glycosides;

f) passing the polishing bed extract stream to a second nanofiltration zone to remove at least a portion of water from the polishing bed extract stream to provide a second nano retentate stream and a second nano permeate stream comprising water; and, g) passing the second nano retentate stream to a drying zone to remove the water and provide a solid steviol glycoside product comprising Rebaudioside D and/or Rebaudioside M and having a sweet steviol glycoside concentration greater than about 95% (w/w) on an anhydrous basis.

In some aspects, the invention relates to method of purifying one or more steviol glycosides (e.g., Rebaudioside D and/or Rebaudioside M) from a mixture, the mixture including the one or more steviol glycosides (e.g., Rebaudioside D and/or Rebaudioside M) and at least one impurity, the method comprising:

passing the mixture through a first adsorbent with a first solvent, the first adsorbent comprising one or more hydrophobic interaction resins or one or more ion exchange resins to provide a first eluate stream, the first eluate stream having the first solvent and a higher purity of the one or more steviol glycosides (e.g., Rebaudioside D and/or Rebaudioside M) than in the mixture as measured by weight percentage of the solid content, and optionally removing at least a portion of the first solvent from the first eluate stream to provide a reduced first eluate stream.

In some aspects, the invention relates to a method of purifying one or more steviol glycosides (e.g., Rebaudioside D and/or Rebaudioside M) from a mixture, the mixture including the one or more steviol glycosides (e.g., Rebaudioside D and/or Rebaudioside M) and at least one impurity, the method comprising:

passing the mixture through a first adsorbent with a first solvent, the first adsorbent comprising one or more hydrophobic interaction resins or one or more ion exchange resins to provide a first eluate stream, the first eluate stream having the first solvent and a higher purity of the one or more steviol glycosides (e.g., Rebaudioside D and/or Rebaudioside M) than in the mixture as measured by weight percentage of the solid content, optionally removing at least a portion of the first solvent from the first eluate stream to provide a reduced first eluate stream, passing the first eluate stream or the reduced first eluate stream through a second adsorbent with a second solvent, the second adsorbent comprising one or more hydrophobic interaction resins or one or more ion exchange resins to provide a second eluate stream, the second eluate stream having the second solvent and a higher purity of the one or more steviol glycosides (e.g., Rebaudioside D and/or Rebaudioside M) than in the first eluate stream or the reduced first eluate stream as measured by weight percentage of the solid content, and optionally removing at least a portion of the second solvent from the second eluate stream to provide a reduced second eluate stream.

In some aspects, the purified product of the present invention comprises a sweet steviol glycoside (e.g., Rebaudioside D and/or Rebaudioside M) concentration greater than about 95% (w/w) on an anhydrous basis.

BRIEF DESCRIPTION OF THE DRAWINGS

The accompanying drawings are included to provide a further understanding of the disclosure. The drawings illustrate embodiments of the disclosure and together with the description serve to explain the principles of the embodiments of the disclosure.

DETAILED DESCRIPTION OF EXEMPLARY EMBODIMENTS

Figure 1:
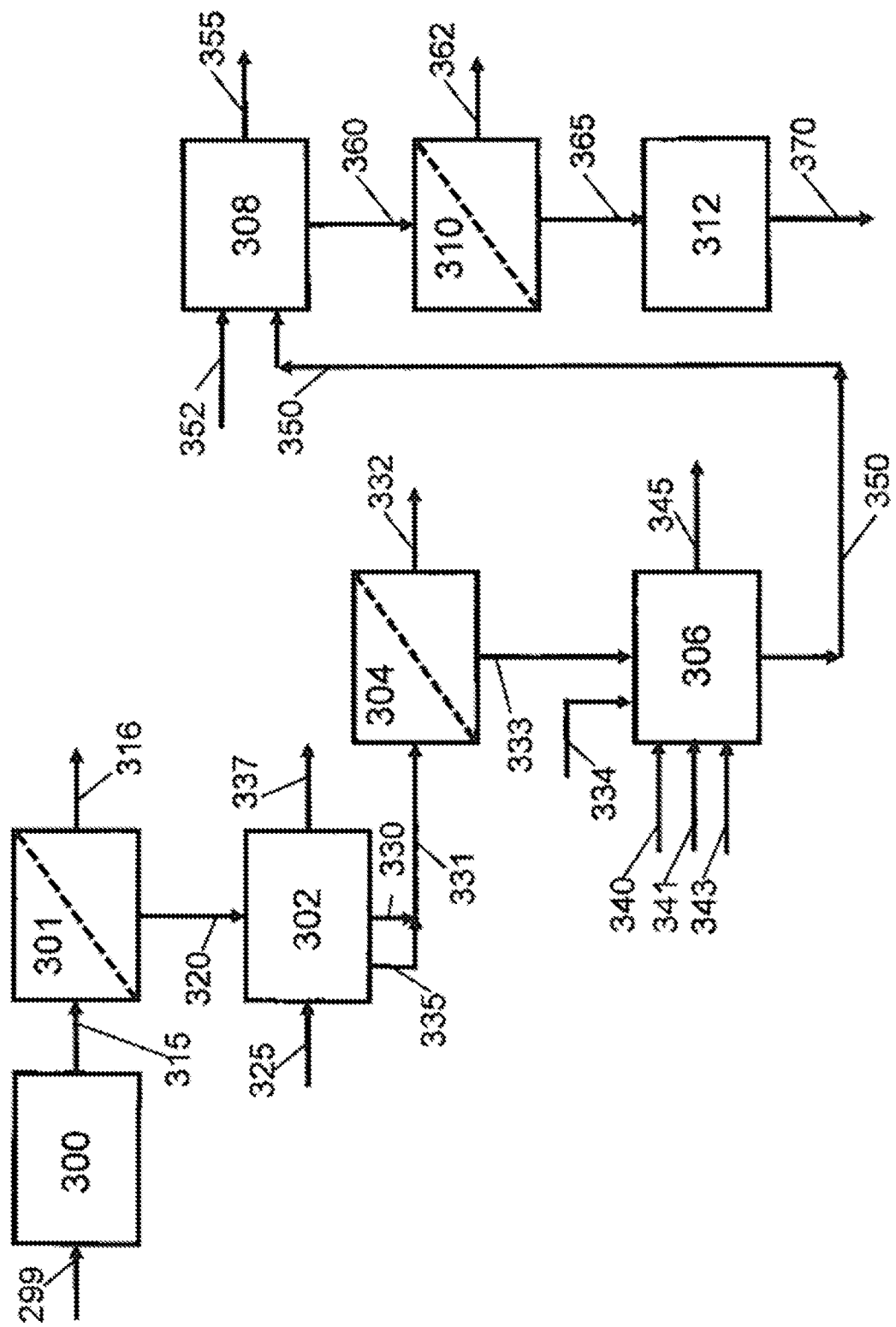
FIG. 1 is a schematic process flow diagram illustrating a configuration of the continuous overall process.

The sweet herb of Paraguay, *Stevia rebaudiana Bertoni*, produces an alternative sweetener with the added advantage that stevia sweeteners are natural plant products. The extract of the *Stevia rebaudiana Bertoni* plant contains a mixture of different sweet diterpene glycosides which have a single base, steviol, and differ by the presence of carbohydrate residues at positions C13 and C19. These steviol glycosides accumulate in stevia leaves and compose approximately 10%-20% of the total dry weight. Typically, on a dry weight basis, the four major glycosides found in the leaves of stevia are Dulcoside A (0.3%), Rebaudioside C (0.6-1.0%), Rebaudioside A (3.8%) and Stevioside (9.1%). Other steviol glycosides identified in Stevia extract include Rebaudiosides B, D, E, F, M, N, and O, Steviolbioside and Rubusoside.

As used herein, the term "stevia" refers to the plant stevia rebaudiana, commonly known as sweetleaf, sweet leaf, sugarleaf, or simply stevia unless otherwise indicated. The phrase "stevia extract" refers to a sweetener-rich extract derived from the leaves of the stevia rebaudiana plant.

As used herein, the phrase "hot water" in the context of an extraction solvent refers generally to water having a temperature of 50° C. to 100° C.

As used herein, the term "steviol glycoside(s)" refers to glycosides of steviol, including, but not limited to, naturally occurring steviol glycosides, e.g. Rebaudioside A, Rebaudioside B, Rebaudioside C, Rebaudioside D, Rebaudioside E, Rebaudioside F, Rebaudioside M, Rebaudioside I, Stevioside, Steviolbioside, Dulcoside A, Rubusoside, etc. or synthetic steviol glycosides, e.g. enzymatically glucosylated steviol glycosides and combinations thereof.

As used herein, the term "total steviol glycosides" (TSG) is calculated as the sum of the content of all steviol glycosides on a dry (anhydrous) basis, including, for example, Rebaudioside A (Reb A), Rebaudioside B (Reb B), Rebaudioside C (Reb C), Rebaudioside D (Reb D), Rebaudioside E (Reb E), Rebaudioside F (Reb F), Rebaudioside G (Reb G), Rebaudioside M (Reb M), Stevioside, Steviolbioside, Dulcoside A and Rubusoside.

Applicant discovered a method of purifying one or more steviol glycosides from a mixture, the mixture including the one or more steviol glycosides and at least one impurity, the method comprising: passing the mixture through a first adsorbent with a first solvent, the first adsorbent comprising one or more hydrophobic interaction resins or one or more ion exchange resins to provide a first eluate stream, the first eluate stream having the first solvent and a higher purity of the one or more steviol glycosides than in the mixture as measured by weight percentage of the solid content, and optionally removing at least a portion of the first solvent from the first eluate stream to provide a reduced first eluate stream. In some embodiments, the method further comprising: passing the first eluate stream or the reduced first eluate stream through a second adsorbent with a second solvent, the second adsorbent comprising one or more hydrophobic interaction resins or one or more ion exchange resins to provide a second eluate stream, the second eluate stream having the second solvent and a higher purity of the one or more steviol glycosides than in the first eluate stream or the reduced first eluate stream as measured by weight percentage of the solid content, and optionally removing at least a portion of the second solvent from the second eluate stream to provide a reduced second eluate stream. In certain embodiments, the method includes one or more of a micro filtration zone, first swing bed simulated moving bed zone, a first nanofiltration zone, second swing bed simulated moving bed zone, a polishing stage simulated moving bed zone, and a second nanofiltration zone provided a scheme wherein water could be employed exclusively as the mobile phase desorbent without requiring the addition of any organic solvent to provide a high purity steviol glycoside product.

In some embodiments, the methods described herein comprise removing one or more solvents. For example, the method can include removing at least a portion of the first solvent from the first eluate stream to provide a reduced first eluate stream and/or removing at least a portion of the second solvent from the second eluate stream to provide a reduced second eluate stream. The solvent can be removed by any suitable method. For example, the solvent can be removed by evaporation (e.g., under reduced pressure, elevated temperature, or a combination thereof), membrane permeation (e.g., nano-filtration), extraction, or a combination thereof.

The methods described herein include purifying one or more steviol glycosides from a mixture. Generally, the one or more steviol glycosides are selected from the group consisting of Dulcoside A, Rebaudioside C, Rebaudioside A, Stevioside, Rebaudioside B, Rebaudioside D, Rebaudioside E, Rebaudioside F, Rebaudioside M, Rebaudioside I, Steviolbioside, and Rubusoside. In preferred embodiments, the one or more steviol glycosides to be purified are Rebaudioside D and/or Rebaudioside M.

The purity of a steviol glycoside (e.g., Rebaudioside D and/or Rebaudioside M) can be measured by any suitable means known to a person of ordinary skill in the art. In some embodiments, the purity of a steviol glycoside (e.g., Rebaudioside D and/or Rebaudioside M) is measured using high performance liquid chromatography (HPLC). In some embodiments, the purity of a steviol glycoside (e.g., Rebaudioside D and/or Rebaudioside M) is assessed using the Joint FAO/WHO Expert Committee on Food Additives (JECFA) method for determining purity. In some embodiments, the purity of a steviol glycoside (e.g., Rebaudioside D and/or Rebaudioside M) is measured using weight percentage of the solid content. If the weight percentage of a constituent in the solid content increases, the constituent is considered to be more pure. If the weight percentage of a constituent in the solid content decreases, the constituent is considered to be less pure. To illustrate, a constituent having a weight percentage of 15% is more pure than if it had a weight percentage of 10%. Similarly, a constituent having a weight percentage of 90% is more pure than if it had a weight percentage of 75%.

As used herein, the term "solid concentration" refers to the mass of solids per volume of liquid in a given stream and is expressed as grams/Liter. The mass of the solids content in a stream is determined by subjecting a fixed volume of the sample, typically 1 ml, to an effective amount of heat, up to 80° C., at atmospheric pressure for a time sufficient to fully evaporate the sample to dryness, typically 1-2 hours.

Methods of the disclosure can use normal-phase chromatography and/or reversed-phase chromatography. In some embodiments, the methods of the disclosure employ a process known as reversed-phase chromatography. As used herein, the term "reversed-phase chromatography" employs a polar (aqueous) mobile phase. As a result, hydrophobic molecules in the polar mobile phase tend to adsorb to the hydrophobic stationary phase, and hydrophilic molecules in the mobile phase will pass through the column and are eluted first. Accordingly, any suitably stationary phase adsorbent (i.e., chromatographic resin) can be used in methods of the disclosure.

In some embodiments, the method comprises passing the mixture through a first adsorbent with a first solvent, the first adsorbent comprising one or more hydrophobic interaction resins or one or more ion exchange (i.e., a cationic resin and/or and anionic resin) resins to provide a first eluate stream. In certain embodiments, the method further comprises passing the first eluate stream or the reduced first eluate stream through a second adsorbent with a second solvent, the second adsorbent comprising one or more hydrophobic interaction resins or one or more ion exchange resins to provide a second eluate stream. Accordingly, the method can include passing a mixture through one or more hydrophobic interaction resins followed by one or more ion exchange (i.e., a cationic resin and/or and anionic resin) resins or passing a mixture through one or more ion exchange (i.e., a cationic resin and/or and anionic resin) resins followed by one or more hydrophobic interaction resins. In preferred embodiments, the first adsorbent is one or more hydrophobic and the second adsorbent is one or more ion exchange (i.e., a cationic resin and/or and anionic resin) resins.

The stationary phase adsorbents may be disposed in a single adsorbent bed or may be disposed in a single column or series of single columns containing multiple adsorbent bed zones. Embodiments of the instant disclosure employ separate stationary phase adsorbents in carrying out the overall process of the disclosure. A list of exemplary stationary phases (i.e., chromatographic resins) for use in various embodiments of the methods of the disclosure are as follows.

The hydrophobic interaction resin can be any suitable hydrophobic interaction resin. In some embodiment, the hydrophobic interaction resin is a porous hydrophobic interaction resin with a particle size of 70-200 microns. In certain embodiments, the hydrophobic interaction resin is a phenylated polymethacrylate polymer resin. Examples of suitable hydrophobic interaction resins having a particle size of about 70-200 microns include TOYOPEARL PHENYL-650C (Available from Tosoh Bioscience, Tokyo, Japan) or RELISORB PH400 (Available from Mitsubishi Chemical Company, Tokyo, Japan). The hydrophobic interaction resin can be used to remove lipids and saccharides as impurities from the steviol glycosides. In certain embodiments, the hydrophobic interaction resin is used in the polishing bed simulated moving bed (SMB) zone, and the lipid and saccharide impurities are rejected into a polishing bed raffinate stream and steviol glycosides are extracted into a polishing bed extract stream.

The ion exchange resin can be any suitable ion exchange (i.e., a cationic resin and/or and anionic resin) resin. In some embodiments, the ion exchange resin is a combination of a cationic resin and an anionic exchange resin. In certain embodiments, the cationic resin and the anionic exchange resin are arranged in series in fluid communication such that the mixture to be purified passes through the cationic resin then the anionic exchange resin or the anionic exchange resin then the cationic exchange resin. The ion exchange resin can be used to remove impurities such as ionic salts, metal ions, flavonoids, pigments, carotenoids, vitamins, proteins, and color bodies. In some embodiments, the ion exchange resin is used in the second swing bed simulated moving bed (SMB) chromatography zone. In the second swing bed simulated moving bed zone, the impurities are retained on the resin and the steviol glycosides are rejected.

In some embodiments, the cationic resin is a styrene-divinylbenzene copolymer resin. In certain embodiments, the cationic resin has an 8 percent cross-linkage with an effective particle size of about 0.5 mm. Suitable examples of the cationic resin include: AMBERLITE IR-118 (Available from Dow Chemical Company, Midland, Mich.), or DIAION PK216LH (Available from Mitsubishi Chemical Company, Tokyo, Japan).

In some embodiments, the anionic resin is an acrylic-divinylbenzene copolymer resin. In certain embodiments, the anionic resin has an effective particle size of about 0.6 mm. Suitable examples of the anionic resin include AMBERLITE IRA-70RF (Available from Dow Chemical Company, Midland, Mich.) or RELITE RAM2 (Available from Mitsubishi Chemical Company, Tokyo, Japan).

In some embodiments, the methods described herein further comprise passing a mixture through an aromatic non-polar copolymer of styrene-divinyl benzene adsorbent resin with an effective particle size of 0.25 mm and effective surface area of 590 $m^2/g$. Examples of suitable styrene-divinyl benzene adsorbent resins can be selected from the AMBERLITE XAD resin series (Available from Dow Chemical Company, Midland, Mich.), DIAION HP-20 (Available from Mitsubishi Chemical Company, Tokyo, Japan), or Stratosphere PL-PS/DVB (Available from Sigma-Aldrich, St. Louis, Mo.). The styrene-divinyl benzene adsorbent resin matrix provides an aromatic non-polar surface with selectivity for hydrophobic areas of molecules. In some embodiments, the styrene-divinyl benzene adsorbent is used in a first swing bed simulated moving bed zone and the steviol glycosides are retained on the resin and are subsequently recovered in a first swing bed extract stream. Impurities such as tri-terpenes, sterols, flavonoids and some of the pigments are rejected into a first swing bed raffinate stream. The stationary phase adsorbents may be disposed in a single adsorbent bed or may be disposed in within a single column or series of single columns containing multiple adsorbent bed zones.

In some embodiments, the methods described herein further include preconditioning an adsorbent prior to use. For example, the methods can include preconditioning the first adsorbent prior to passing the mixture through a first adsorbent with a first solvent and/or preconditioning the second adsorbent prior to passing the first eluate stream or the reduced first eluate stream through a second adsorbent with a second solvent. As used herein, the term preconditioning refers to a method of washing an adsorbent and/or equilibrating an adsorbent at a particular temperature or flow rate. In some embodiments, preconditioning comprises washing with acid, base, water, or a combination thereof.

In some embodiments, the method comprises purifying a steviol glycoside (e.g., Rebaudioside D and/or Rebaudioside M) with simulated moving bed (SMB) chromatography. In some embodiments, the method relates to a continuous process for the purification of steviol glycosides, specifically Rebaudioside D and/or Rebaudioside M using a sequence of purification steps and a continuous simulated moving bed process and downstream recovery steps to separate Rebaudioside D and/or Rebaudioside M.

The SMB system of the current invention was arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The SMB system may be operated such that the adsorbent beds are operated individually or in parallel using a single rotary valve and associated control system. A column may comprise one or several beds containing chromatographic media. Those feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art.

In some embodiments, a simulated moving bed (SMB) system is arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process in some embodiments. Feed and mobile phase desorbent enter, while extract and raffinate streams are withdrawn continuously at substantially constant compositions. The overall operation is similar in performance to an operation wherein the fluid and solid are contacted in a continuous countercurrent manner, without the actual movement of the solid, or stationary phase adsorbent.

In some embodiments, the method comprises passing a mixture through a SMB zone to provide a primary raffinate stream. The SMB zone comprises a plurality of adsorbent beds (e.g., columns comprising a stationary phase). The SMB zone can comprises any suitable number of adsorbent beds. For example, the SMB zone can comprise 2 or more adsorbent bed, e.g., 3 or more adsorbent beds, 4 or more adsorbent beds, 5 or more adsorbent beds, 6 or more adsorbent beds, 10 or more adsorbent beds, or 20 or more adsorbent beds. In some embodiments, the plurality of adsorbent beds are arranged in serial fluid communication such that fluid introduced at a top of any adsorbent bed (n) passes to the next highest adsorbent bed (n+1). In such embodiments, the method can further comprise advancing each adsorbent bed, such that adsorbent bed n+1 becomes adsorbent bed n after advancing, and adsorbent bed n prior to advancing becomes adsorbent bed n+x after advancing, wherein adsorbent bed n+x is the highest adsorbent bed in the serial fluid communication arrangement.

In some embodiments, the SMB zone comprises eight adsorbent beds. The eight adsorbent beds can be broken down into four zones referring to a desorption zone, a rectification zone, an adsorption zone, and a concentration zone. The adsorbent beds can be in any suitable arrangement (e.g., 2-2-2-2, 3-2-2-1, 2-3-2-1, 2-2-3-1, 1-3-3-1, 3-3-1-1, 3-1-3-1, or 2-2-3-1, etc.), wherein each number refers to one of the four zones. In certain embodiments, the SMB zone is in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a regeneration zone, respectively.

In some embodiments, the first adsorbent is arranged in a SMB configuration to form a first SMB zone, and wherein passing the mixture through the through the first adsorbent with the first solvent comprises passing the mixture through the first SMB zone.

In some embodiments, the second adsorbent is arranged in a SMB configuration to form a second SMB zone, and wherein passing the first eluate stream or the reduced first eluate stream through the second adsorbent with the second solvent comprises passing the first eluate stream or the reduced first eluate stream through the second SMB zone.

The mobile phase desorbent or solvent (e.g., first solvent and second solvent) of the present invention for use in all of the purification methods comprises water, preferably deionized water. Accordingly, the mobile phase desorbent or solvent can comprise an additional solvent such as ethanol, acetone, ethyl acetate, acetonitrile, pentanes, hexanes, heptanes, methanol, propanol, or a combination thereof. In some embodiments, the mobile phase desorbent (e.g., the first solvent and the second solvent) comprise greater than 95% v/v water. In certain embodiments, the mobile phase desorbent (e.g., the first solvent and the second solvent) comprise greater than 99% v/v water. In preferred embodiments, the mobile phase desorbent (e.g., the first solvent and the second solvent) are water (i.e., do not contain an additional solvent).

The mixture of steviol glycosides can be obtained by any suitable means. For example, the mixture can be obtained from a stevia plant extract, a stevia fermentation broth, a yeast fermentation broth, an *Escherichia coli* fermentation broth, or an enzyme-converted mixture. Accordingly, in addition to obtaining a naturally occurring mixture from extraction of a stevia plant such as *Stevia rebaudiana Bertoni*, the mixture of steviol glycosides can be obtained from recombinant production systems or enzymatic conversion reactions. Without wishing to be bound by any particular theory, it is believed that recombinant production systems or enzymatic conversion reactions can be utilized to produce an increased abundance of steviol glycosides and/or a preferred distribution of particular steviol glycosides.

An exemplary procedure for purification of the extract from a stevia plant such as *Stevia rebaudiana Bertoni* is as follows: following harvesting and processing, the grinded and dried stevia leaves are extracted with an appropriate GRAS solvent or hot water. A number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material: solvent (v/v)) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results. Following the extraction of the steviol glycosides from the stevia leaves, an extract stream comprising crude steviol glycosides is withdrawn from the extraction zone. Preferably, the crude steviol glycosides are admixed with water to provide a crude extract stream which comprises from about 34 wt. % to about 40 wt. % total steviol glycosides in the aqueous mixture. More preferably, the crude extract stream comprises from about 34 wt. % to about 37 wt. % total steviol glycosides in the aqueous mixture. The concentration of solids in the crude extract stream varies from about 60 to about 80 g/L and is preferably about 75 g/L.

In some embodiments, the crude extract stream (i.e., mixture to be purified) is obtained from a yeast fermentation broth. In certain embodiments where the crude extract stream (i.e., mixture to be purified) is obtained from a yeast fermentation broth, the mixture comprises from about 15 wt. % to about 30 wt. % total steviol glycosides. Alternatively, or additionally, the crude extract stream (i.e., mixture to be purified) obtained from a yeast fermentation broth can have a concentration of solids from 20 mg/mL to about 50 mg/mL. In some embodiments, the crude extract stream (i.e., mixture to be purified) is obtained from an *Escherichia coli* fermentation broth. In certain embodiments where the crude extract stream (i.e., mixture to be purified) is obtained from an *Escherichia coli* fermentation broth, the mixture comprises from about 5 wt. % to about 15 wt. % total steviol glycosides. Alternatively, or additionally, the crude extract stream (i.e., mixture to be purified) obtained from an *Escherichia coli* fermentation broth can have a concentration of solids from 20 mg/mL to about 50 mg/mL.

In some embodiments, a mixture described herein (e.g., the crude extract stream) is passed to a microfiltration zone to remove any solid particles to provide a filtered extract stream. The microfiltration can be carried at a microfiltration temperature ranging from about 50° C. to about 60° C. and the microfilter in the microfiltration zone can range from about 0.2 μm to about 0.5 μm. Preferably, the microfilter pore size in the microfiltration zone comprises a microfilter pore size about 0.2 μm.

In some embodiments, a mixture described herein (e.g., the crude extract stream) is nanofiltered. Nanofiltration is a membrane filtration-based method that uses nanometer sized cylindrical through-pores that pass through the membrane at 90°. Nanofiltration membranes have pore sizes from 1-10 nanometers, smaller than that used in microfiltration and ultrafiltration, but just larger than that in reverse osmosis. Membranes used are predominantly created from polymer thin films. Materials that are commonly use include polyethylene terephthalate or metals such as aluminum. The nano filter pore size employed in the nanofiltration zones of present invention range from about 100 to 300 Da (Dalton). The pore size of a nanofiltration membrane in the nanofiltration zone characterized by a cut-off value. This cut-off value is consistent with the molecular weight of the smallest molecule that can be 90% restricted by the top layer of the membrane. The cut-off value of the nanofiltration membrane is typically expressed in Dalton (Dalton=weight in grams of mole of the molecule). More preferably, the pore size in the first nanofiltration zones is less than 150 Da. The nanofiltration is employed to remove excess water from extract streams withdrawn from simulated moving bed zones to obtain a target concentration of steviol glycosides in the effluent from the nanofiltration zone.

Figure 2:
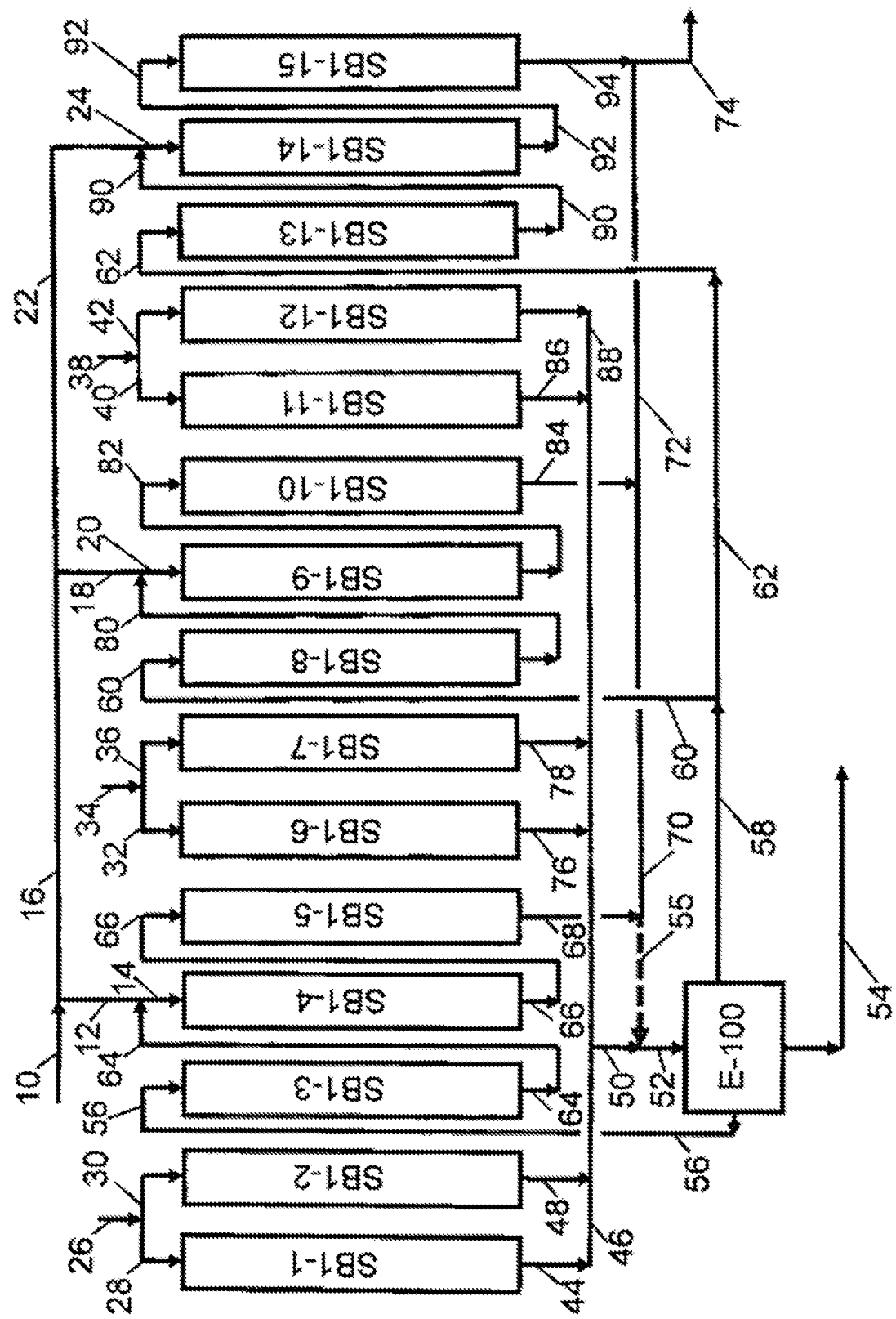
FIG. 2 is a schematic process flow diagram illustrating a configuration of the simulated moving bed cycle for a First Swing Bed simulated moving bed zone in one embodiment of the invention.

According to one embodiment of the invention and with reference to FIG. 1, dried stevia leaves from the *Stevia rebaudiana Bertoni*, plant are passed in line 299 to an extraction zone 300 and therein admixed with an effective amount of hot water (not shown) and agitated by conventional means to provide a crude steviol extract stream which is withdrawn in line 315. The crude steviol extract stream in line 315 is passed to a microfiltration zone 301 to remove at least a portion of solid particles and provide a filtered crude extract stream in line 320 and a first waste water stream in line 316. The microfiltration zone contains an extract filter which is a micro-filter having a 0.2 µm filter. Typically, the filtered crude extract stream comprises about 34-40 wt % total steviol glycosides on an anhydrous basis. The feed concentration of total steviol glycosides in the filtered extract stream comprises about 75 grams/liter. The filtered extract stream comprises sweet steviol glycosides (e.g., Rebaudioside D and/or Rebaudioside M), other steviol glycosides, water, tri-terpenes, sterols, flavonoids, volatile oils, pigments, gums, proteins, carotenoids, chlorophyll, vitamins and saccharides, solid insolubles and salts. The overall process is continuous process along with nanofiltration units and water recovery plant. The process is carried out at a process operating temperature of the overall process ranging from about 50° C. to about 80° C. More preferably, the process is carried out at a process operating temperature of the overall process ranging from about 60° C. to about 80° C. Most preferably, the process is carried out at a process operating temperature which should not exceed 80° C. The desorbent used in the process is deionized water (DI water) having a pH of between about 6 and about 7, and having an electrical conductivity less than 5 µS/cm. The filtered crude extract stream in line 320 is passed to a first Swing Bed simulated moving bed zone 302 and the first waste water stream is passed to a waste water recovery zone (not shown). The first Swing Bed simulated moving bed zone 302 is further described hereinbelow in connection with FIG. 2. As shown in FIG. 2, the first Swing Bed simulated moving bed zone 302 consists of 15 first swing adsorbent beds, a rotary valve, an arrangement of valves and piping, and a valve control system. Each of the first swing adsorbent beds contain a first swing bed resin consisting of an aromatic, non-polar copolymer of styrene-divinyl benzene adsorbent resin. The first swing bed resin provides an aromatic non-polar surface with selectivity for hydrophobic areas of molecules for use in a simulated moving bed system based on hydrophobic interaction chromatography. In the first swing bed simulated moving bed zone, essentially all of the steviol glycosides are adsorbed on the first swing bed resin and impurities such as chlorophyll, sterols, volatile oils, tri-terpenes, volatile oils, carotenoids, vitamins and gum are rejected in aqueous first swing bed raffinate streams. The first swing bed mobile phase desorbent is water which is introduced in line 325 to provide a primary first Swing Bed raffinate stream in line 335, a secondary first Swing Bed raffinate stream in line 337, and a first Swing Bed extract stream in line 330. The primary first Swing Bed raffinate stream in line 335 is collected in the first half of each step of the first swing bed cycle, and the secondary first Swing Bed raffinate stream in line 337 is collected during the second or remaining portion of each step. The secondary first swing bed raffinate stream is essentially a waste stream which is continuously withdrawn and passed to a waste water recovery zone (not shown) comprising a reverse osmosis zone for recovery of water for use in the process. The primary first Swing Bed raffinate stream in line 335 and the first Swing Bed extract stream in line 330 are combined to provide the first swing bed extract stream in line 331. The first swing bed extract stream in line 331 is passed to a first nanofiltration zone 304, having a nano filter pore size of about 100 to 300 Da (Dalton), and wherein the first swing bed extract stream is concentrated to provide a first nano retentate stream in line 333 and a first nano permeate stream in line 332. The pore size of a nanofiltration membrane in the first nanofiltration zone 304 is characterized by a cut-off value. This cut-off value is consistent with the molecular weight of the smallest molecule that can be 90% restricted by the top layer of the membrane. The cut-off value of the nanofiltration membrane is typically expressed in Dalton (Dalton=weight in grams of mole of the molecule). More preferably, the pore size in the first nanofiltration zone 304 is less than 150 Da. The first nano permeate stream in line 332 is passed to the waste water recovery zone (not shown). The first nano retentate stream in line 333 and a second mobile phase desorbent stream comprising or consisting of water in line 334 are passed to a second swing bed simulated moving bed zone 306. The second Swing Bed simulated moving bed zone 306 is further described hereinbelow in connection with FIG. 3. The second swing Bed simulated moving bed zone 306 comprises a first series of second swing adsorbent beds which are serially connected adsorbent beds through which the first nano retentate stream in line 333 and the second mobile phase desorbent line 334 are passed, wherein during each of the steps of the second swing bed SMB cycle, at least one second swing adsorbent bed is charged or loaded with the first nano retentate stream for a portion of the step, after which the first series of serially connected second swing adsorbent beds are washed by passing the second mobile phase desorbent stream to wash the second swing adsorbent beds to provide a second swing bed elute stream in line 350 comprising water and essentially all of the steviol glycosides (e.g., Rebaudioside D and/or Rebaudioside M). The second series of second swing adsorbent beds are separately washed in isolation by introducing an acid wash stream in line 340, a basic wash stream in line 341, and a water wash stream in line 343 to regenerate the second swing adsorbent beds and to provide a second swing bed raffinate stream in line 345. The second swing bed raffinate stream in line 345 comprises waste water which is passed to the water recovery zone (not shown) for water recovery. The second swing bed extract stream in line 350 and a polishing bed mobile phase desorbent stream in line 352 consisting or containing water are passed to a polishing bed zone 308. The polishing bed zone 308 comprises a series of polishing bed adsorbent beds operated as a simulated moving bed system, and include at least 15 polishing bed adsorbent beds, a valve control system, a rotary valve, and associated piping. The polishing bed zone 308 is further described hereinbelow in connection with FIG. 4. In one embodiment, the polishing bed adsorbent beds are divided into at least two sections. The first section and the second section each comprise three zones. The polishing bed zone provides a polishing bed extract stream in line 360 and a polishing zone total raffinate stream in line 355. The polishing zone total raffinate stream in line 355 is passed to the waste water recovery zone (not shown) for recovery of water for use in the process. The polishing bed extract stream in line 360 is passed to a second nanofiltration zone 310 to provide a filtered polished extract stream in line 365 and a second nano permeate stream in line 362. The pore size of the nanofiltration membrane in the second nanofiltration zone 310 is characterized by a cut-off value of 100 to 300 Da. More preferably, the pore size of the nanofiltration membrane in the second nanofiltration zone 310 is less than 150 Da. The filtered polished extract stream in line 362 is passed to a spray drying zone 312 to remove water in a conventional manner and provide a dry stevia product in line 370 comprising essentially the desired steviol glycosides (e.g., Rebaudioside D and/or Rebaudioside M). The dry stevia product can comprise the desired steviol glycosides (e.g., Rebaudioside D and/or Rebaudioside M) in a concentration ranging from 92 to 95 wt. % on an anhydrous basis. More preferably, the dry stevia product comprises the desired steviol glycosides (e.g., Rebaudioside D and/or Rebaudioside M) concentration greater than or equal to 95 wt. % on an anhydrous basis. The dry stevia product may be in the form of powder, aggregates or pellets.

In some embodiments, and with reference to FIG. 2, the first swing bed simulated moving bed system (SB1) is a continuous simulated moving bed system which continuously processes the filtered crude extract stream in line 10 to provide a first swing bed elute stream in line 54. The first swing bed simulated moving bed system (SB1) comprises a plurality of first swing adsorbent beds wherein the plurality of first swing adsorbent beds are separated into at least three identical sections which are operated in parallel, and each section comprises three zones. Each adsorbent bed has a top and a bottom and each first swing adsorbent bed contains a selective adsorbent being a non-polar copolymer styrene-divinylbenzene adsorbent resin and being a spherical particle with a 0.5 mm diameter. An example of such a non-polar resin is DIAION™ HP-20 (Available from Mitsubishi Chemical Corporation, Japan). With reference to FIG. 2, adsorbent beds SB1-1 through SB1-5 comprise the first SB1 section, first swing adsorbent beds SB1-6 through SB1-10 comprise the second SB1 section, and SB1-11 through SB1-15 comprise the third SB1 section. Within the first SB1 section, the first mobile phase desorbent comprising or consisting of deionized water in line 26 is passed to the top of zone 1 of section 1 (adsorbent beds SB1-1 and SB1-2) via line 26 and lines 28 and 30 to the top of adsorbent beds SB1-1 and SB1-2, respectively. In section 1, zone 1, the mobile phase desorbent is passed to the top of first swing adsorbent beds SB1-1 and SB1-2 via lines 28 and 30, respectively, to provide a first swing bed elute, which is withdrawn from the bottom of first swing adsorbent beds SB1-1 and SB1-2 in lines 44 and 48, respectively, and passed via elute header 46 to a first swing bed elute surge tank E-100 via lines 50 and 52. In zone 2 of section 1, a portion of the first swing bed elute is withdrawn from first swing bed elute surge tank E-100 via line 56 and passed to the top of zone 2 of section 1 or first swing adsorbent bed SB1-3 and the effluent of first swing adsorbent bed SB1-3 is passed via line 64 to be admixed with a portion of the filtered extract stream which is introduced via line 10 and lines 12, and the admixture passed via line 14 to the top of zone 3 of section 1. In zone 3 of section 1, first swing adsorbent beds SB1-4 and SB1-5 are arranged in serial fluid communication, whereby the effluent from the bottom of first swing adsorbent bed SB1-4, an extract recycle stream, is passed to the top of first swing adsorbent bed SB1-5 in line 66, and a first swing bed raffinate stream is withdrawn from the bottom of adsorbent bed SB1-5 via line 68. During each step of the first swing bed SMB cycle, for the first portion of the step, a first portion of the first swing bed raffinate stream in line 68 is passed via lines 68, 55 and 52 to be admixed with the first swing bed elute in the first swing bed elute surge tank E-100. In the second or remaining portion of each step of the first swing bed SMB cycle, a secondary swing bed raffinate is withdrawn from SB1-5 as a first swing bed secondary raffinate stream and passed via lines 68, 70, 72, and 74 to provide a net first swing bed secondary raffinate stream in line 74 which is a waste water stream and may be passed to waste water recovery (not shown). Similarly, in the second SB1 section, first mobile phase desorbent comprising or consisting of deionized water in line 34 is passed to zone 1 of section 2 via line 34. In section 2, zone 1, the first mobile phase desorbent is passed to the top of adsorbent beds SB1-6 and SB1-7 via lines 32 and 36, respectively, to provide first swing bed elute, which is withdrawn for the bottom of adsorbent beds SB1-6 and SB1-7 in lines 76 and 78, respectively, and passed via elute header 46 to the first swing bed elute surge tank E-100 via lines 50 and 52. In zone 2 of section 2, a portion of the first swing bed elute is withdrawn from first swing bed elute surge tank E-100 via lines 58 and 60 and passed to the top of zone 2 of section 2 or adsorbent bed SB1-8, and the effluent of adsorbent bed SB1-8 is passed via line 80 to be admixed with a portion of the filtered extract stream which is introduced via line 10, 16 and line 18, and the admixture passed via line 20 to the top of zone 3 of section 2. In zone 3 of section 2, first swing adsorbent beds SB1-9 and SB1-10 are arranged in serial fluid communication whereby the effluent from the bottom of first swing adsorbent bed SB1-9 is passed to the top of first swing adsorbent bed SB1-10 in line 82, and the first swing bed raffinate stream is withdrawn from the bottom of first swing adsorbent bed SB1-10 via line 84. During each step of the first swing bed SMB cycle, for the first portion of each step, the first portion of the first swing bed primary raffinate stream in line 84 is passed via lines 84, 70, 55 and 52 to be admixed with the first swing bed elute in the first swing bed elute surge tank E-100. In the second or remaining portion of each of the first swing bed steps, the secondary swing bed raffinate is withdrawn from first swing adsorbent bed SB1-10 as a first swing bed secondary raffinate stream and passed via lines 84, 72, and 74 to provide net first swing bed secondary raffinate stream in line 74 which is an SB1 waste water stream and may be passed to waste water recovery (not shown). Similarly, in the third SB1 section, first mobile phase desorbent comprising or consisting of deionized water in line 38 is passed to zone 1 of section 3 via line 38. In section 3, zone 1, the first mobile phase desorbent is passed to the top of first swing adsorbent beds SB1-11 and SB1-12 via lines 40 and 42, respectively, to provide a first swing bed elute, which is withdrawn for the bottom of first swing adsorbent beds SB1-11 and SB1-12 in lines 86 and 88, respectively, and passed via elute header 46 to a first swing bed elute surge tank E-100 via lines 50 and 52. In zone 3 of section 1, a portion of the first swing bed elute is withdrawn from first swing bed elute surge tank E-100 via lines 58 and 62, and passed to the top of zone 2 of section 3 or first swing adsorbent bed SB1-13 and the effluent of adsorbent bed SB1-13 is passed via line 90 to be admixed with a portion of the filtered extract stream which is introduced via lines 10, 16 and 22, and the admixture passed via line 24 to the top of first swing adsorbent bed SB1-14 in zone 3 of section 3. In zone 3 of section 3, first swing adsorbent beds SB1-14 and SB1-15 are arranged in serial fluid communication, whereby the effluent from the bottom of first swing adsorbent bed SB1-14 is passed to the top of first swing adsorbent bed SB1-15 in line 92, and the first swing bed raffinate stream is withdrawn from the bottom of first swing adsorbent bed SB1-15 via line 94 and passed to the first swing bed secondary raffinate header (line 74). During each step of the first swing bed SMB cycle, for the first portion of each step of the first swing bed SMB cycle, a portion of the first swing bed raffinate stream in line 94 is passed via lines 94, 72, 70, 55 and 52 to be admixed with the first swing bed elute in the first swing bed elute surge tank E-100. In the second or remaining portion of each of the steps the first swing bed SMB cycle, the secondary swing bed raffinate is withdrawn from first swing adsorbent bed SB1-15 as a first swing bed secondary raffinate stream and passed via lines 94 and 74 to provide a portion of the first swing bed secondary raffinate stream in line 74 which is a waste water stream and may be passed to waste water recovery (not shown). At the completion of each of the steps of the first swing bed SMB cycle, the rotary valve is sequenced to increment each first swing adsorbent bed by one position to the left in a counterclockwise manner, whereby SB1-15 is moved to the position of SB1-14, and so on, and SB1-1 is moved to the position previously occupied by SB1-15.

In certain embodiments, the first swing bed simulated moving bed zone has a plurality of first swing adsorbent beds which are disposed in one or more clockwise, sequentially disposed sections. Each section comprises five first swing adsorbent beds and separated into 3 zones, wherein a zone 1 comprises the first two first swing adsorbent beds which are desorbed with a portion of the first mobile phase desorbent to provide a portion of the first swing extract stream, a zone 2 comprising the third first swing adsorbent bed, which is loaded with a portion of the first mobile phase desorbent to provide a portion of an extract recycle stream. The portion of an extract recycle stream is admixed with the filtered crude extract stream and passed to the fourth and fifth first swing adsorbent beds to load the first swing adsorbent and to provide a portion of the primary first swing bed raffinate stream during a first portion of a simulated moving bed step and a portion of the secondary first swing bed raffinate stream during a second or remaining portion of a simulated moving bed step. At the completion of each of the steps of the first swing bed SMB cycle, a rotary valve is sequenced to increment each first swing adsorbent bed by one position to the left in a counterclockwise manner.

Figure 3:
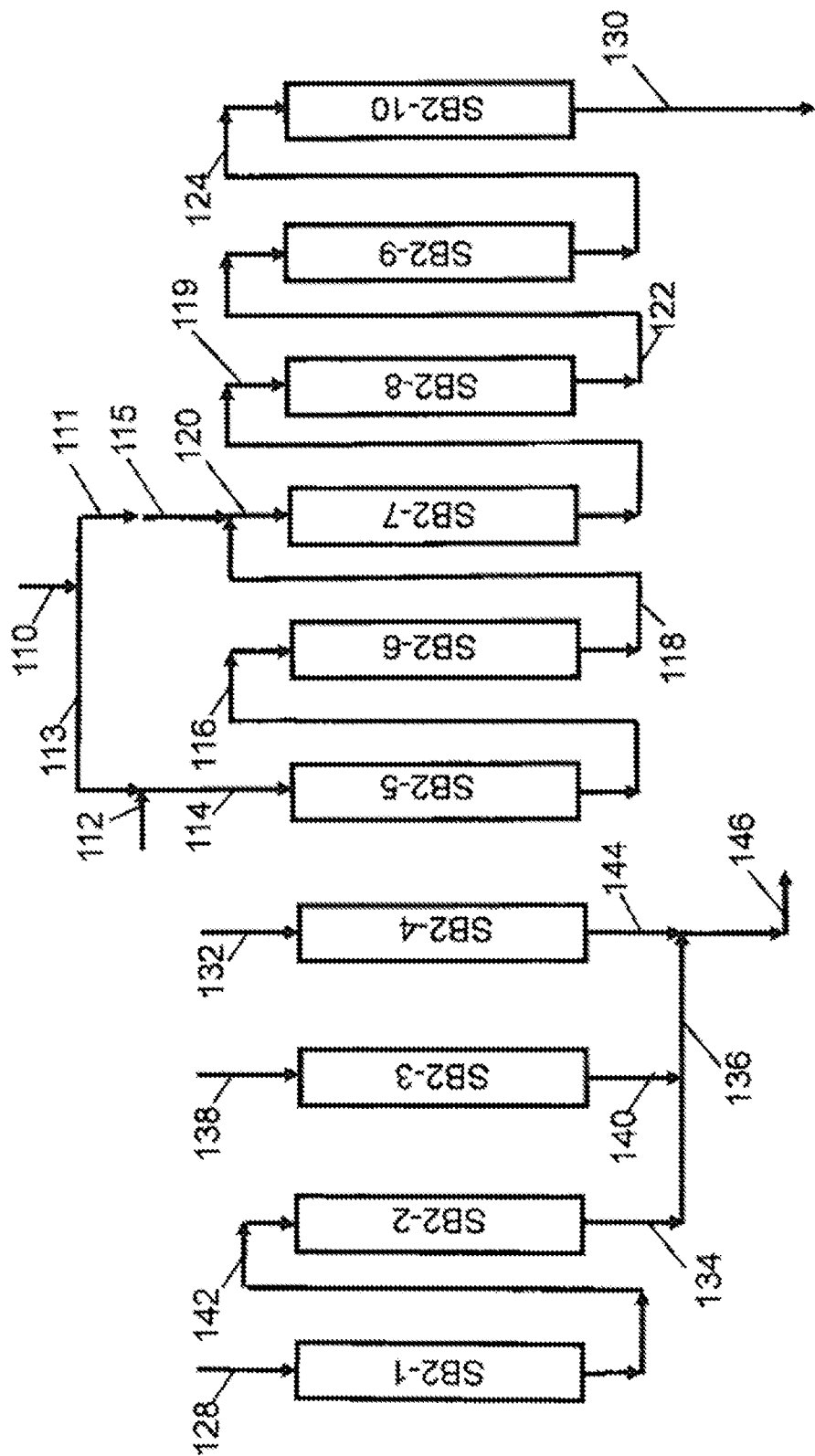
FIG. 3 is a schematic process flow diagram illustrating a configuration of the simulated moving bed cycle for a Second Swing Bed simulated moving bed zone in one embodiment of the invention.

In some embodiments, and with reference to FIG. 3, the second swing bed simulated moving bed system is a continuous simulated moving bed system which continuously processes the first swing bed elute stream after nanofiltration, or first nano retentate stream, in line 110 and a second mobile phase desorbent stream in line 112 to provide a second swing bed elute stream in line 130. The second swing bed simulated moving bed system (SB2) comprises a plurality of second swing adsorbent beds wherein the plurality of second swing adsorbent beds are separated into an adsorption/desorption section (SB2-5-SB2-10) and a regeneration section (SB2-1-SB2-4). As shown in FIG. 3, second swing adsorbent beds SB2-5 through SB2-10 represent the adsorption/desorption zone of the second swing bed simulated moving bed system (SB2) wherein second swing adsorbent beds SB2-5 through SB2-10 are second swing adsorbent beds and contain a selective adsorbent as described hereinabove and each second swing adsorbent bed has a top and a bottom. In one embodiment, the second swing adsorbent beds alternately contain either a strongly acidic cationic resin or a weakly basic anionic resin. For example, the odd numbered adsorbent beds (SB2-1, SB2-3, SB2-5, SB2-7, and SB2-9) contain a strongly acidic cationic resin and the even numbered adsorbent beds (SB2-2, SB2-4, SB2-6, SB2-8, and SB2-10) contain a weakly basic anionic resin. In the adsorption/desorption zone, second swing adsorbent beds SB2-5 through SB2-10 are in serial fluid communication wherein the effluent of SB2-5 is passed from the bottom of second swing adsorbent bed SB2-5 to the top of second swing adsorbent bed SB2-6 via line 116; the effluent of second swing adsorbent bed SB2-6 is passed from the bottom of second swing adsorbent bed SB2-6 to the top of second swing adsorbent bed SB2-7 via lines 118 and 120; the effluent of SB2-7 is passed from the bottom of second swing adsorbent bed SB2-7 to the top of second swing adsorbent bed SB2-8 via line 119; the effluent of second swing adsorbent bed SB2-8 is passed from the bottom of second swing adsorbent bed SB2-8 to the top of second swing adsorbent bed SB2-9 via line 122; and, the effluent of SB2-9 is passed from the bottom of second swing adsorbent bed SB2-9 to the top of second swing adsorbent bed SB2-10 via line 124. The second swing bed elute stream in line 130 is withdrawn from the bottom of second swing adsorbent bed SB2-10. The second swing bed elute stream comprises steviol glycosides and is essentially free of ionic impurities such as salts and proteins. By the term essentially free of ionic impurities the second swing bed elute stream contains less than about 0.5 wt. % ionic impurities on an anhydrous basis.

In some embodiments of the second swing bed SMB cycle, the nanofiltered elute stream in line 110 is introduced to SB2-5 via lines 110, 113 and 114 and to SB2-7 via lines 110, 111, and 115 and 120 for a portion of each step in a loading step, after which for the remainder of each step, the adsorbent beds (SB2-5-SB2-10) are serially and sequentially washed with the second mobile phase desorbent comprising or consisting of water introduced in lines 112 and 114 to adsorbent bed SB2-5 to provide a second swing bed extract stream in line 130. The SB2 regeneration section (SB2-1-SB2-4) operates essentially in parallel carrying out a series of regeneration steps which include:

(1) a serial water wash zone wherein a adsorbent beds SB2-1 (cation) and SB2-2 (anion) pair of adsorbent beds are water washed by passing a second water wash stream in line 128 to the top of adsorbent bed SB2-1, withdrawing the wash effluent from adsorbent bed SB2-1 in line 142 and passing the wash effluent to the top of adsorbent bed SB2-2 and withdrawing a first SB2 waste water stream I line 134;

(2) a basic/acidic regeneration zone wherein adsorbent bed SB2-3, containing the strongly acidic cation adsorbent is subjected to a four part regeneration procedure wherein (a) adsorbent bed SB2-3 is washed with an aqueous basic solution such as sodium hydroxide having an NaOH concentration of from about 2 grams/100 ml water to about 4 grams/100 ml water NaOH (a NaOH concentration ranging from a 0.5N to 1N NaOH solution), (b) washed with a water wash stream in a first regeneration wash step, (c) washed with an aqueous mild acid solution such as HCl having an HCl concentration of from about 2 ml HCl per 100 ml water to about 4 ml HCl per 100 ml water (an HCl concentration of from 0.2 to 0.6 N HCl solution) to reactivate the adsorbent, and (d) washed in a second water wash with the water wash stream; and (3) an basic regeneration zone wherein adsorbent bed SB2-4, containing the weakly basic anion adsorbent is subjected to a two part regeneration procedure wherein (a) adsorbent bed SB2-4 is washed with an aqueous basic solution such as sodium hydroxide having an NaOH concentration of from about 2 grams/100 ml water to about 4 grams/100 ml water NaOH (a NaOH concentration ranging from a 0.5N to 1N NaOH solution), and (b) washed in a second water wash with the water wash stream.

All of the parts of the above series of four part regeneration streams are introduced to adsorbent bed SB2-3 sequentially in line 138 and a regeneration zone effluent stream is withdrawn in line 140 as a second SB2 waste water stream. Second swing adsorbent bed SB2-4 is sequentially washed by passing a basic solution via line 132 to the top of second swing adsorbent bed SB2-4, followed by washing the second swing bed adsorbent bed SB-2-4 with a water wash stream introduced in line 132 to provide a third SB2 waste water stream line 144. The basic solution in line 132 is an aqueous basic solution wherein the base is an alkali metal such as sodium, and the base is sodium hydroxide having a concentration ranging between about 2 grams/100 ml water to about 4 grams/100 ml water (a NaOH concentration ranging from a 0.5N to 1N NaOH solution). The first waste water stream in line 134, the second SB2 waste water stream in line 140, and the third waste water stream in line 144 are collected in line 146 as a total SB2 waste water stream and passed to the waste water recovery zone (not shown). In the operation of the second swing bed simulated moving bed system (SB2), the second swing adsorbent beds are moved in cation/anion pairs. Thus, at the completion of each step of the second swing bed SMB cycle, the rotary valve is sequenced to increment each second swing adsorbent bed by two positions (n+2) to the left in a counterclockwise manner, whereby second swing adsorbent beds SB2-3 and SB2-4 are moved to the position of second swing adsorbent beds SB2-1 and SB2-2, and so on; and second swing adsorbent beds SB2-1 and SB2-2 are moved to the positions previously occupied by second swing adsorbent beds SB2-9 and SB2-10.

Figure 4:
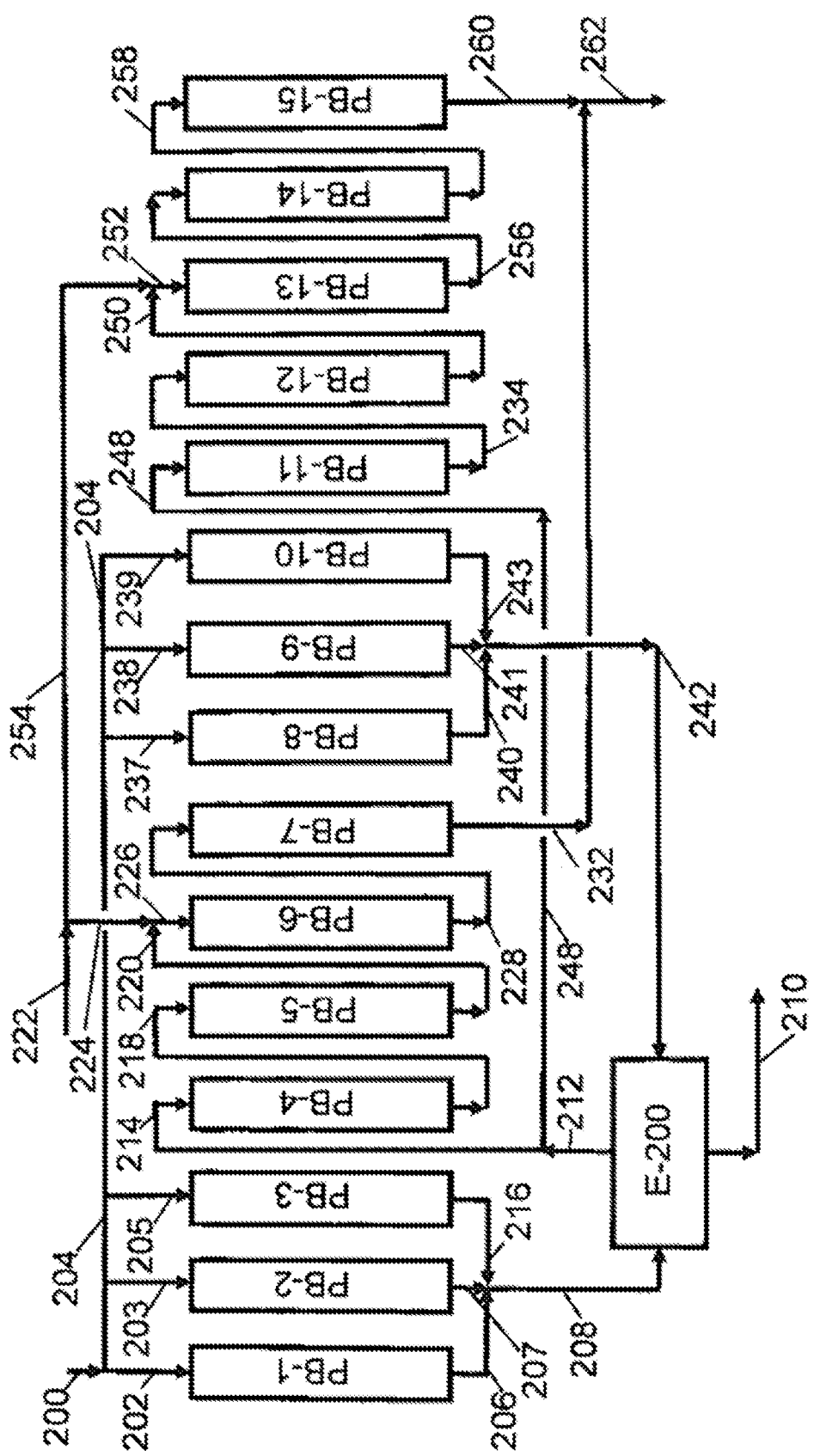
FIG. 4 is a schematic process flow diagram illustrating a configuration of the simulated moving bed cycle for a Polishing Bed simulated moving bed zone in one embodiment of the invention.

According to one embodiment of the invention and with reference to FIG. 4, the polishing bed simulated moving bed system is a continuous simulated moving bed system which continuously processes the second swing bed extract stream in line 222 to provide a polishing bed extract stream or purified steviol glycoside stream in line 210. With reference to FIG. 4, the polishing bed simulated moving bed system comprises a plurality of polishing bed adsorbent beds containing a selective adsorbent. Each of the polishing bed adsorbent beds has a top and a bottom. The polishing bed adsorbent beds may be sequentially disposed linearly or sequentially disposed about a circumference of a circle. The plurality of polishing bed adsorbent beds are separated or grouped into at least two identical sections which are operated in parallel. The polishing bed simulated moving bed zone is shown with 15 polishing bed adsorbent beds (PB-1 to PB-15), wherein the first section, or section A includes polishing bed adsorbent beds PB-1, PB-2, PB-3, PB-4, PB-5, PB-6, and PB-7, and a second section, section B includes polishing bed adsorbent beds PB-8, PB-9, PB-10, PB-11, PB-12, PB-13, PB-14 and PB-15. Each Section contains 3 zones (1, 2, and 3). The first PB zone, zone 1, is a desorption zone wherein upon introduction of desorbent, an extract is removed. The second PB zone, zone 2 is a separation zone, wherein steviol glycosides are adsorbed and separated from fatty acids, saccharides, and phospholipids. In the third PB zone, zone 3, or loading zone, the second swing bed extract is loaded on to the polishing bed adsorbent beds in zone 3 and the polishing bed raffinate is withdrawn. The polishing bed is typically configured with one or more sections wherein each polishing bed zone has at least two polishing bed adsorbent beds, and each section has a 3-2-2 arrangement having 3 polishing bed adsorbent beds in the desorption zone, 2 polishing bed adsorbent beds in the separation zone, and 2 polishing bed adsorbent beds in the loading zone, or a 3-2-3 arrangement having 3 polishing bed adsorbent beds in the desorption zone, 2 polishing bed adsorbent beds in the separation zone, and 3 polishing bed adsorbent beds in the loading zone. Preferably there are at least two or more polishing bed adsorbent beds in the loading zone. Thus a polishing bed SMB system having one section could include 7 or 8 polishing bed adsorbent beds, having two sections could include 14 or 15 polishing bed adsorbent beds, or having three sections could include 21-24 polishing bed adsorbent beds. The desorbent is introduced to the top of zone 1 wherein the desorbent contacts the hydrophobic adsorbent and extract is withdrawn from zone 1. A portion of the extract is recycled to zone 2, and the effluent of zone 2 is admixed with the elute stream from the second swing bed simulated moving bed system (SB2) before being passed to zone 3. The effluent from zone 3 is raffinate. Referring to FIG. 4, the third mobile phase desorbent stream comprising or consisting of deionized water in line 200 is passed to the top of zone 1 of section A which comprises polishing bed adsorbent beds PB-1, PB-2, and PB-3 that are arranged in parallel, wherein the mobile phase desorbent is simultaneously introduced to the top of polishing bed adsorbent bed PB-1 via line 200 and 202, to the top of adsorbent bed PB-2 via lines 200, 204 and 203, and top of polishing bed adsorbent bed PB-3 via lines 200, 204 and 205 to provide a zone 1 effluent stream from adsorbent bed PB-1, which is withdrawn from the bottom of polishing bed adsorbent bed PB-1 in line 206, from polishing bed adsorbent bed PB-2 which is withdrawn from the bottom of polishing bed adsorbent bed PB-2 in line 207, and from polishing bed adsorbent bed PB-3 which is withdrawn from the bottom of polishing bed adsorbent bed PB-3 in line 216, and passed as a section A extract stream to a polishing bed extract surge tank E-200 in line 208 to provide a pooled extract stream in the extract surge tank E-200. At least a portion of the pooled extract stream from the polishing bed extract surge tank E-200 is withdrawn via lines 212 and 214 and passed to the top of section A zone 2 comprising polishing bed adsorbent beds PB-4 and PB-5. Polishing bed adsorbent beds PB-4 and PB-5 are arranged in serial fluid communication wherein the at least a portion of the section A extract stream is introduced to the top of polishing bed adsorbent bed PB-4 via line 214 and a first zone 2 effluent from adsorbent bed PB-4 is withdrawn from the bottom of polishing bed adsorbent bed PB-4 and passed in line 218 to the top of polishing bed adsorbent bed PB-5. A second section A zone 2 effluent stream in line 220 is withdrawn from the bottom of polishing bed adsorbent bed PB-5 as the Section A zone 2 effluent stream in line 220 and passed to the top of section A zone 3 which comprises polishing bed adsorbent beds PB-6 and PB-7. The Section A zone 2 effluent stream in line 220 is admixed with a second swing bed extract stream, or polishing bed zone feed stream introduced via lines 222 and 224 to provide a feed mixture in line 226 which is passed to the top of section A, zone 3. Section A zone 3 comprises polishing bed adsorbent beds PB-6 and PB-7 which are in serial fluid communication wherein the polishing bed feed stream is passed to the top of polishing bed adsorbent bed PB-6 in line 226 and an intermediate section A zone 3 stream is withdrawn from the bottom of polishing bed adsorbent bed PB-6 in line 228 and passed to the top of polishing bed adsorbent bed PB-7 and the effluent from polishing bed adsorbent bed PB-7 or the first section polishing bed raffinate stream in line 232 is withdrawn from polishing bed adsorbent bed PB-7 as a portion of the total polishing bed raffinate stream in line 262. The polishing bed raffinate stream is considered a waste water stream and is passed to waste water treatment for recovery of water. The mobile phase desorbent mixture in line 200 is passed to the top of zone 1 of section B via mobile phase desorbent header 204 and lines 237, 238 and 239 to polishing bed adsorbent beds PB-8, PB-9 and PB-10, respectively. Polishing bed adsorbent beds PB-8, PB-9 and PB-10 make up zone 1 of section B and are arranged in parallel whereby the mobile phase desorbent is introduced to the top of polishing bed adsorbent beds PB-8, PB-9 and PB-10 to provide a section B zone 1 effluent stream which is withdrawn from the bottom of polishing bed adsorbent beds PB-8, PB-9 and PB-10, in lines 240, 241, and 243, respectively, and which are combined in line 242 and passed to the polishing bed extract surge tank E-200 to provide the pooled extract stream in the extract surge tank E-200. At least a portion of the section B extract stream is passed to the top of section B zone 2 via lines 212 and 248. Section B zone 2 comprises polishing bed adsorbent beds PB-11 and PB-12 which are in serial fluid communication. A section B zone 2 intermediate stream is withdrawn from the bottom of polishing bed adsorbent bed PB-11 and passed to the top of polishing bed adsorbent bed PB-12 via line 234 to provide a section B zone 2 effluent stream in line 250 which is withdrawn from the bottom of polishing bed adsorbent bed PB-12 and passed to the top of section B zone 3, polishing bed adsorbent beds PB-13, PB-14 and PB-15. Polishing bed adsorbent beds PB-13, PB-14 and PB-15 are arranged in serial fluid communication wherein the portion of the section B zone 2 effluent stream in line 250 is combined with the extract stream is introduced to the top of polishing bed adsorbent bed PB-11 and a first section B zone 2 effluent from polishing bed adsorbent bed PB-11 is withdrawn from the bottom of adsorbent bed PB-11 and passed in line 234 to the top of polishing bed adsorbent bed PB-12. A second section B zone 2 effluent stream in line 250 is withdrawn from the bottom of polishing bed adsorbent bed PB-12 and passed to the top of polishing bed adsorbent bed PB-13. The section B zone 2 effluent stream in line 250 is admixed with a portion of the second swing bed extract stream, or polishing bed zone feed stream introduced via lines 222 and 254 to provide a feed mixture in line 256 which is passed to the top of section B, zone 3. Section B zone 3 comprises polishing bed adsorbent beds PB-13, PB-14 and PB-15 which are in serial fluid communication wherein feed mixture in line 256 is passed to the top of polishing bed adsorbent bed PB-13, and an intermediate section B zone 3 stream is withdrawn from the bottom of polishing bed adsorbent bed PB-13 in line 256, and passed to the top of polishing bed adsorbent bed PB-14. A second intermediate section B zone 3 stream is withdrawn from the bottom of polishing bed adsorbent bed PB-14 in line 258, and passed to the top of polishing bed adsorbent bed PB-15. A polishing bed raffinate stream in line 260 is withdrawn from polishing bed adsorbent bed PB-15 and is combined with section A zone 2 raffinate in line 232 to provide a total polishing bed raffinate stream in line 262. At the completion of each cycle, the rotary valve is sequenced to increment each polishing bed adsorbent bed by one position to the left in a counterclockwise manner, whereby PB-2 is moved to the position of PB-1, and so on, and PB-1 is moved to the position previously occupied by the last bed in the polishing bed SMB system, PB-15. At least a portion of the pooled extract stream the surge tank E-200 is withdrawn to provide the polishing bed extract stream or purified steviol glycoside stream in line 210. The polishing bed raffinate stream in line 262 is considered a fourth waste water stream and is passed to waste water treatment (not shown) for recovery of water.

In one embodiment, in the polishing bed zone, the plurality of polishing bed adsorbent beds is disposed in one or more clockwise, sequentially disposed sections. Each section has a desorption zone, a separation zone and a loading zone. In the operation of each section of the polishing bed zone; a portion of the third mobile phase desorbent is passed to the desorption zone to provide a portion of the polishing bed extract stream; a portion of the polishing bed extract stream is passed to the separation zone to provide a separation zone effluent stream; and, a portion of the polishing bed extract stream is admixed with the second swing bed elute stream to provide a portion of the polishing bed raffinate stream. At the completion of each of step of a polishing bed SMB cycle, a rotary valve is sequenced to increment each polishing bed adsorbent bed by one position to the left in a counterclockwise manner.

EMBODIMENTS

Principles of the present disclosure are incorporated in the following embodiments:

Embodiment (1) A method of purifying one or more steviol glycosides from a mixture, the mixture including the one or more steviol glycosides and at least one impurity, the method comprising: passing the mixture through a first adsorbent with a first solvent, the first adsorbent comprising one or more hydrophobic interaction resins or one or more ion exchange resins to provide a first eluate stream, the first eluate stream having the first solvent and a higher purity of the one or more steviol glycosides than in the mixture as measured by weight percentage of the solid content, and optionally removing at least a portion of the first solvent from the first eluate stream to provide a reduced first eluate stream.

Embodiment (2) The method of embodiment (1), the method further comprising: passing the first eluate stream or the reduced first eluate stream through a second adsorbent with a second solvent, the second adsorbent comprising one or more hydrophobic interaction resins or one or more ion exchange resins to provide a second eluate stream, the second eluate stream having the second solvent and a higher purity of the one or more steviol glycosides than in the first eluate stream or the reduced first eluate stream as measured by weight percentage of the solid content, and optionally removing at least a portion of the second solvent from the second eluate stream to provide a reduced second eluate stream.

Embodiment (3) The method of embodiment (1), wherein the one or more steviol glycosides are selected from the group consisting of Dulcoside A, Rebaudioside C, Rebaudioside A, Stevioside, Rebaudioside B, Rebaudioside D, Rebaudioside E, Rebaudioside F, Rebaudioside M, Rebaudioside I, Steviolbioside, and Rubusoside.

Embodiment (4) The method of embodiment (1), wherein the one or more steviol glycosides are Rebaudioside D and Rebaudioside M.

Embodiment (5) The method of embodiment (1), wherein the one or more steviol glycosides is Rebaudioside D.

Embodiment (6) The method of embodiment (1), wherein the one or more steviol glycosides is Rebaudioside M.

Embodiment (7) The method of embodiment (1), wherein the mixture is a stevia plant extract, a stevia fermentation broth, a yeast fermentation broth, an *Escherichia coli* fermentation broth, or an enzyme-converted mixture.

Embodiment (8) The method of embodiment (7), wherein the stevia plant is *Stevia rebaudiana Bertoni*.

Embodiment (9) The method of embodiment (2), wherein the first solvent and the second solvent comprise water.

Embodiment (10) The method of embodiment (9), wherein the first solvent and the second solvent comprise greater than 95% v/v water.

Embodiment (11) The method of embodiment (10), wherein the first solvent and the second solvent comprise greater than 99% v/v water.

Embodiment (12) The method of embodiment (11), wherein the first solvent and the second solvent are water.

Embodiment (13) The method of embodiment (1), wherein said at least one impurity comprises at least one of tri-terpenes, sterols, flavonoids, volatile oils, pigments, gums, proteins, carotenoids, chlorophyll, vitamins, phospholipids, saccharides, solid insoluble, salts, fermentation byproducts, or N-acetyl glucosamine.

Embodiment (14) The method of embodiment (4), wherein said at least one impurity comprises a second steviol glycoside selected from Dulcoside A, Rebaudioside C, Rebaudioside A, Stevioside, Rebaudioside B, Rebaudioside E, Rebaudioside F, Rebaudioside I, Steviolbioside, Rubusoside, and combinations thereof.

Embodiment (15) The method of embodiment (2), wherein the first adsorbent is one or more hydrophobic interaction resins.

Embodiment (16) The method of embodiment (15), wherein the one or more hydrophobic interaction resins is a phenylated polymethacrylate polymer resin.

Embodiment (17) The method of embodiment (16), wherein the phenylated polymethacrylate polymer resin has a particle size of from about 75 μm to about 200 μm.

Embodiment (18) The method of embodiment (15), wherein the second adsorbent is one or more ion exchange resins.

Embodiment (19) The method of embodiment (18), wherein the one or more ion exchange resins is a combination of a cationic resin and an anionic resin.

Embodiment (20) The method of embodiment (19), wherein the cationic resin and anionic resin are arranged in series.

Embodiment (21) The method of embodiment (19), wherein the cationic resin is a styrene-divinylbenzene copolymer resin and the anionic resin is an acrylic-divinylbenzene copolymer resin.

Embodiment (22) The method of embodiment (1), wherein the first adsorbent is arranged in a SMB configuration to form a first SMB zone, and wherein passing the mixture through the through the first adsorbent with the first solvent comprises passing the mixture through the first SMB zone.

Embodiment (23) The method of embodiment (2), wherein the second adsorbent is arranged in a SMB configuration to form a second SMB zone, and wherein passing the first eluate stream or the reduced first eluate stream through the second adsorbent with the second solvent comprises passing the first eluate stream or the reduced first eluate stream through the second SMB zone.

Embodiment (24) The method of embodiment (1), the method further comprising: preconditioning the first adsorbent prior to passing the mixture through a first adsorbent with a first solvent.

Embodiment (25) The method of embodiment (24), wherein preconditioning comprises washing with acid, base, water, or a combination thereof.

Embodiment (26) The method of embodiment (2), the method further comprising: preconditioning the second adsorbent prior to passing the first eluate stream or the reduced first eluate stream through a second adsorbent with a second solvent.

Embodiment (27) The method of embodiment (26), wherein preconditioning comprises washing with acid, base, water, or a combination thereof.

Embodiment (28) The method of embodiment (2), the method further comprising: drying the second eluate stream or the reduced second eluate stream.

The foregoing exemplary embodiments of the disclosure numbered 1-28 are non-limiting. Other exemplary embodiments are apparent from the entirety of the description herein. As will be apparent to those of skill in the art upon reading this disclosure, each of the individually numbered embodiments may be used or combined with any of the preceding or following individually numbered aspects.

EXAMPLES

The following examples are provided to illustrate the present disclosure. These examples are shown for illustrative purposes, and any disclosures embodied therein should not be limited thereto.

Example 1—First Swing Bed Simulated Moving Bed Zone

The removal of a portion of the impurities, such as tri-terpenes, sterols, flavonoids and some of the pigments, from the filtered crude extract stream was demonstrated in an SMB unit in a configuration operating as the first swing bed simulated moving bed zone. A lab scale SMB unit (OCTAVE-300 unit, available from Semba Biosciences, Inc. Madison, Wis.) was used for separation of steviol glycosides from impurities including: tri-terpenes, sterols, flavonoids, and some of the pigments. The Semba Octave-300 Chromatography System is a bench top automated liquid chromatography platform designed for preparative-scale purification of chemical and biological compounds. The Octave System carries eight column positions arranged in series and connected through a proprietary pneumatic valve array. The independently working and programmable 72-valve array contains no moving parts, occupies only 3 μl per valve, and responds within 100 ms. Fluid flow is controlled by four independent pumps. The valve switching and pump flow rates are controlled via the SembaPro Software. Five adsorbent beds, each comprising a SS316 column having an inside diameter of 50 mm and a length of 600 mm were packed with about 960 grams of DIAION HP-20 resin, styrene-divinyl benzene adsorbent resin (Available from Mitsubishi Chemical Company, Tokyo, Japan).

According to the configuration in FIG. 2, the above five adsorbent beds were disposed in an arrangement illustrated by adsorbent beds SB1-1, SB1-2, SB1-3, SB1-4 and SB1-5, representing the first section of the three section unit shown in FIG. 2. In each column set, the feed (filtered crude stevia extract) was loaded in Zone 3 (SB1-4 and SB1-5) via lines 10, 12, and 14. Zone 3 consisted two adsorbent beds (SB1-4 and SB1-5) connected in series. During each step, only one column in zone 3 received the feed. In Zone 3, at least a portion of the impurities from the feed (filtered crude extract stream) were removed with the effluent from Zone 3 as a raffinate stream and the steviol glycosides were retained on the adsorbent. The effluent from Zone 3 was divided into a first swing bed primary raffinate stream and a secondary first swing bed raffinate stream. The first swing bed primary raffinate stream was collected from Zone 3 during the first portion of each step in the SMB cycle, and the first swing bed secondary raffinate stream was collected during the remaining portion of each step. A switch valve controlled the effluent stream flow direction. The first swing bed secondary raffinate stream was essentially a waste stream and was continuously sent for waste disposal or waste water recovery. The first swing bed primary raffinate stream was combined with the SB1 extract (line 44) withdrawn from SB1-1 and SB1 extract withdrawn from SB1-2 (line 48) as the SB1 extract stream (line 54). The SB1 desorbent (water in line 26) was loaded on to the adsorbent beds in Zone 1 (SB1-1 and SB1-2) in parallel (lines 28 and 30). The effluent from Zone 1 is called SB1 Extract 1 (line 44) and SB1 Extract 2 (line 48) and passed to an extract tank (via header 46 and lines 50 and 52). In Zone 1, essentially all of the steviol glycosides are recovered from the adsorbent beds and following desorption with water were fully regenerated. A portion of the SB1 Extract 1 is partially loaded back into Zone 2 (via line 56). Table 2 shows the SMB operating parameters for the operation of the first swing bed simulated moving bed zone.

TABLE 2

SMB Operating Parameters-First Swing Bed SMB

| PARAMETER | VALUE | UNIT |
|---|---|---|
| Step Time | 18.0 | Minutes |
| Bath Temperature | 62 | ° C. |
| Feed Rate (line 10)* | 1.5 | L/HR |
| Desorbent (line 28) | 8.0 | L/HR |
| Desorbent (line 30) | 7.1 | L/HR |
| Zone 2 (SB1-3, line 56) | 3.4 | L/HR |
| Extract (line 44) | 4.7 | L/HR |
| Extract (line 48) | 7.1 | L/HR |
| Primary Raffinate (line 68, 55) | 2.4 | L/HR |
| Secondary Raffinate (line 68, 70) | 2.4 | L/HR |

*Line numbers refer to FIG. 2

The desorbent or mobile phase was low conductivity RO (reverse osmosis) water (20-50 micro Siemens). The adsorbent beds were arranged in a water bath having a temperature range of 55-70° C., and was maintained at an average bath temperature of ranging from 62-65° C. Analysis of the feed and products was carried out by high performance liquid chromatography. The samples were analyzed on a 3 µm, OROSIL C18, a reverse phase C18 column having an interior diameter of 4.6 mm and a length of 150 mm (Available from Orochem Technologies, Inc., Naperville, Ill.), at 40° C. using a mobile phase comprising a solution of 10 mM Sodium phosphate, a pH of 2.6, acetonitrile (69:31, v/v), and a flow rate of 0.6 ml/min. The concentration of sweet steviol glycosides (Rebaudioside A (A), Stevioside (S), and Rebaudioside C(C)) in the total SB1 extract was 66 wt. % on an anhydrous basis, and the recovery of total steviol glycosides based on the feed to the First Swing Bed SMB was 90% on a weight basis (w/w).

Figure 5:
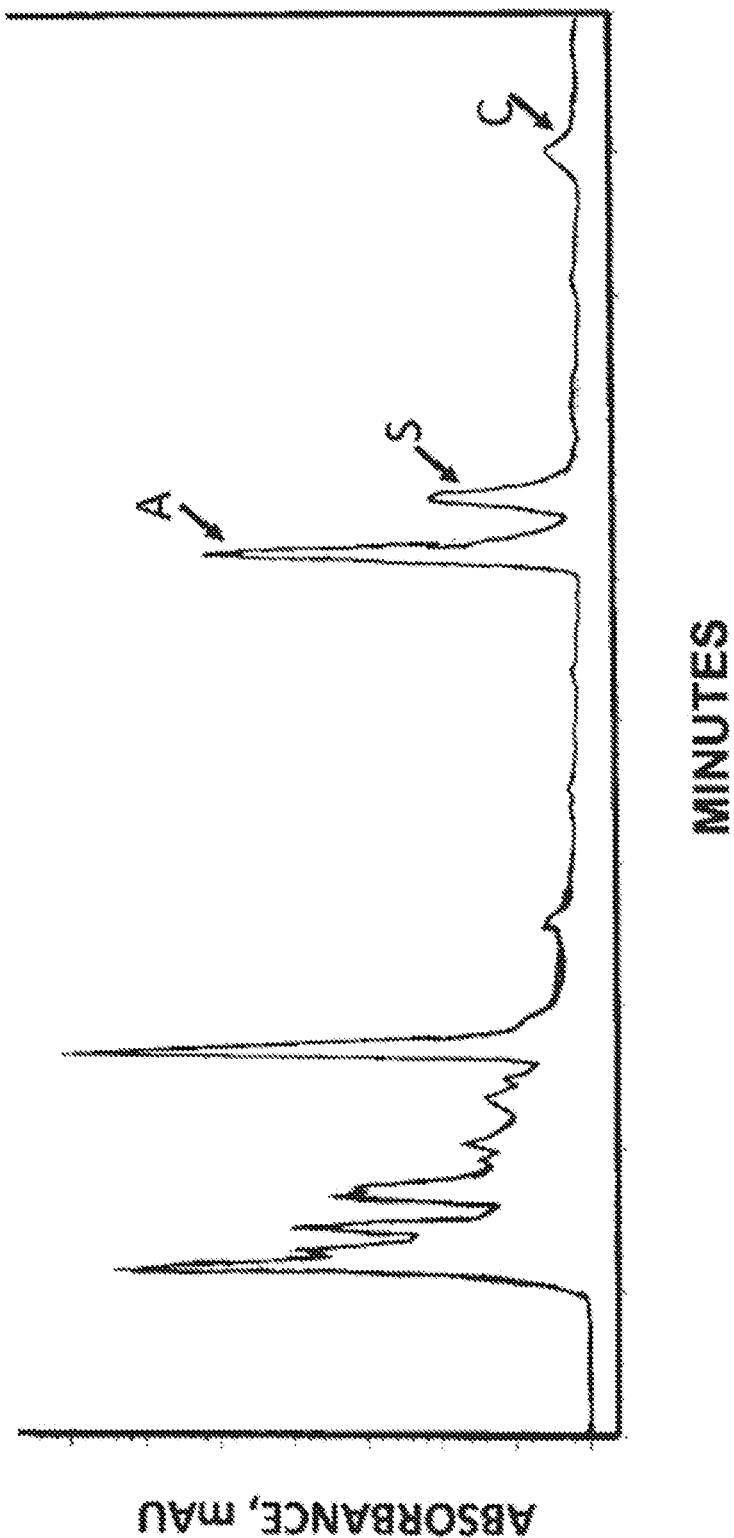
FIG. 5 is a High Performance Liquid Chromatography (HPLC) chromatographic area plot of the composition analysis of the crude stevia extract.

FIG. 5 is a High Performance Liquid Chromatography (HPLC) chromatographic area plot of the composition of crude stevia extract showing the results of a composition analysis of the crude steviol glycoside which following microfiltration with a 0.2 µm filter was the feed to the first swing bed simulated moving bed zone. The impurities appear to the left of center and the predominant sweet steviol glycosides: Rebaudioside A (A), Stevioside(S), Rebaudioside C(C) appear to the right of center.

Figure 6:
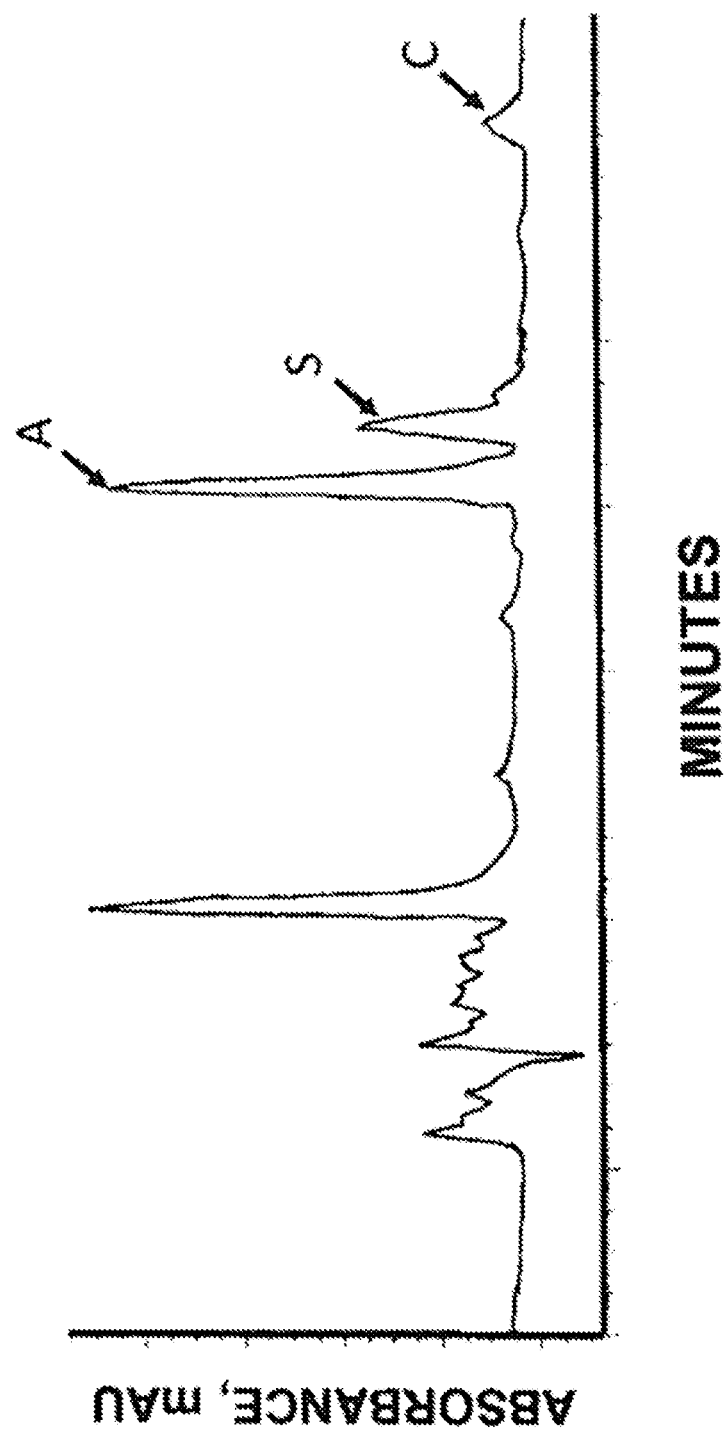
FIG. 6 is a High Performance Liquid Chromatography (HPLC) chromatographic area plot showing the results of a composition analysis of the extract stream withdrawn from the First Swing Bed simulated moving bed zone of the present invention.

FIG. 6 is a High Performance Liquid Chromatography (HPLC) chromatographic area plot showing the results of a composition analysis of the extract stream withdrawn from the First Swing Bed simulated moving bed zone which when compared to FIG. 5, showed the reduction of a portion of the impurities, such as tri-terpenes, sterols, flavonoids and some of the pigments, from the filtered crude extract stream.

Example 2—Second Swing Bed Simulated Moving Bed Zone

The first swing bed (SB1) extract stream withdrawn from the first swing bed simulated moving bed zone of Example 1 was concentrated by nanofiltration to provide a concentrated extract having a dry mass of about 75 g/l. The first swing bed extract stream comprises essentially all of the steviol glycosides in the crude steviol plant extract, nonionic impurities, and ionic impurities such as salts and proteins. The second swing bed employed alternating cationic and anionic resin zones to separate the ionic impurities from steviol glycosides. The second swing bed (SB2) consisted of a plurality of adsorbent beds connected in series, wherein every other adsorbent bed contained a cation or an anion resin. Six chlorinated polyvinyl chloride columns, each having an inside diameter of 100 mm (4 inches) and a length of 914 mm (36 inches) were each loaded alternately in pairs with about 5600 grams of a strongly acidic cation exchange porous styrene-divinylbenzene copolymer bead resin, DIAION PK216LH (Available from Mitsubishi Chemical Company, Tokyo, Japan), or with a weakly basic anion exchange porous acrylic-divinylbenzene copolymer bead resin, RELITE RAM2 (Available from Mitsubishi Chemical Company, Tokyo, Japan) and are connected in series fluid communication as shown in FIG. 3, for SB2-5, SB2-6, SB2-7, SB2-8, SB2-9, SB2-10. The adsorbent beds were arranged in a water bath having a temperature range of 55-70° C., and was maintained at an average bath temperature of ranging from 62-65° C. The columns were first washed with DI water (2 bed volumes) and the concentrated extract having a dry mass of about 75 g/l was loaded on to the columns at a feed rate of 300 ml/min. After loading a total of 20 liters on to the columns, the feed loading was stopped. Water was then introduced via line 112 and 114 to wash the serial arrangement of adsorbent beds with DI water at a flow rate of 300 ml/min, introducing a total volume of 25 liters of water to desorb the adsorbed steviol glycosides to provide second swing bed elute stream in line 130 comprising steviol glycosides, having a steviol glycoside concentration of about 25 g/l on an anhydrous basis, and having a reduced amount of ionic impurities such as salt and proteins relative to the crude steviol extract. By the term essentially free of ionic impurities the second swing bed elute stream contains less than about 0.5 wt. % ionic impurities on an anhydrous basis. The second swing bed elute stream comprising sweet steviol glycosides had a concentration of 85 wt. % Rebaudioside A (A), Stevioside (S), and Rebaudioside C(C) with a steviol glycoside recovery of 98 wt. % (w/w) relative to the first swing bed (SB1) extract stream.

Figure 7:
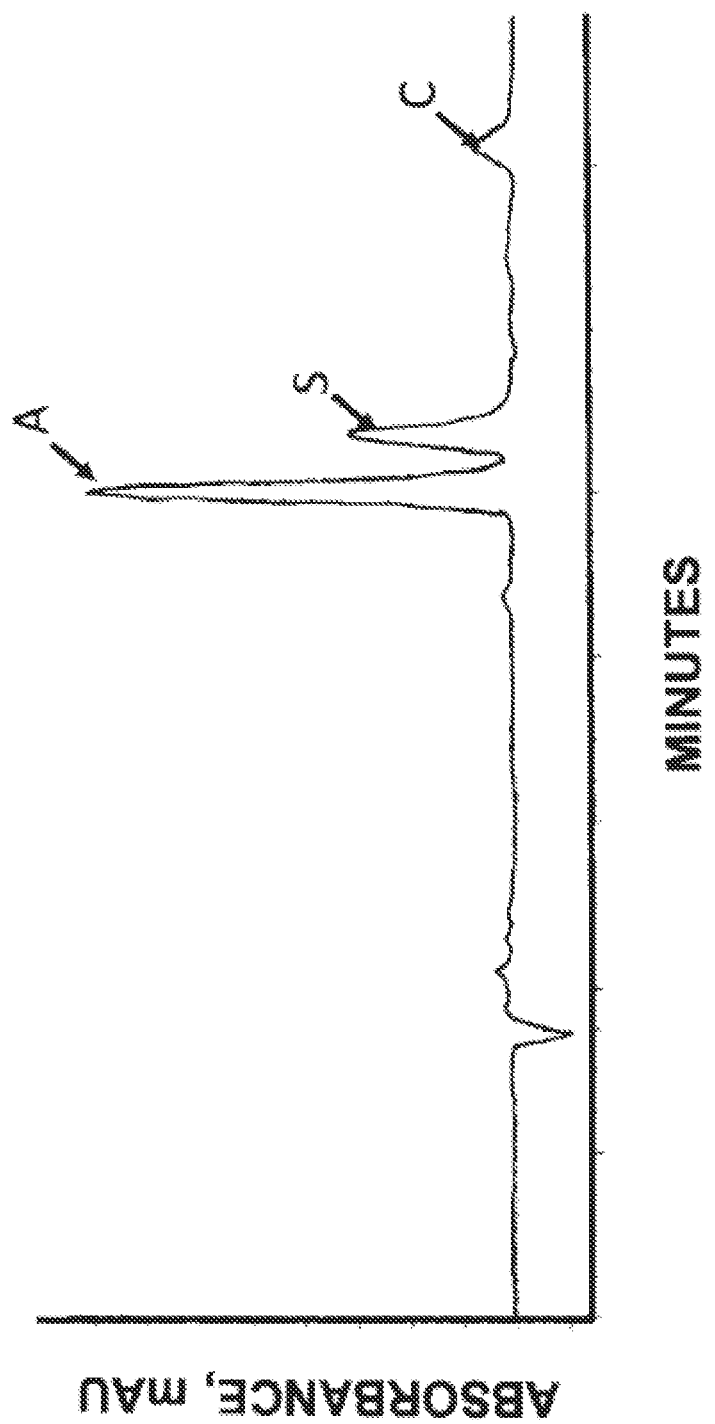
FIG. 7 is a High Performance Liquid Chromatography (HPLC) chromatographic area plot showing the results of a composition analysis of the second extract stream withdrawn from the Second Swing Bed simulated moving bed zone of the present invention.

FIG. 7 is a High Performance Liquid Chromatography (HPLC) chromatographic area plot showing the results of a composition analysis of the second extract stream withdrawn from the Second Swing Bed simulated moving bed zone which shows the further purification of the steviol glycosides, comprising sweet steviol glycosides: Rebaudioside A, Stevioside, Rebaudioside C, and nonionic impurities including fatty acids and sugars.

Example 3—Polishing Bed Simulated Moving Bed Zone

Figure 8:
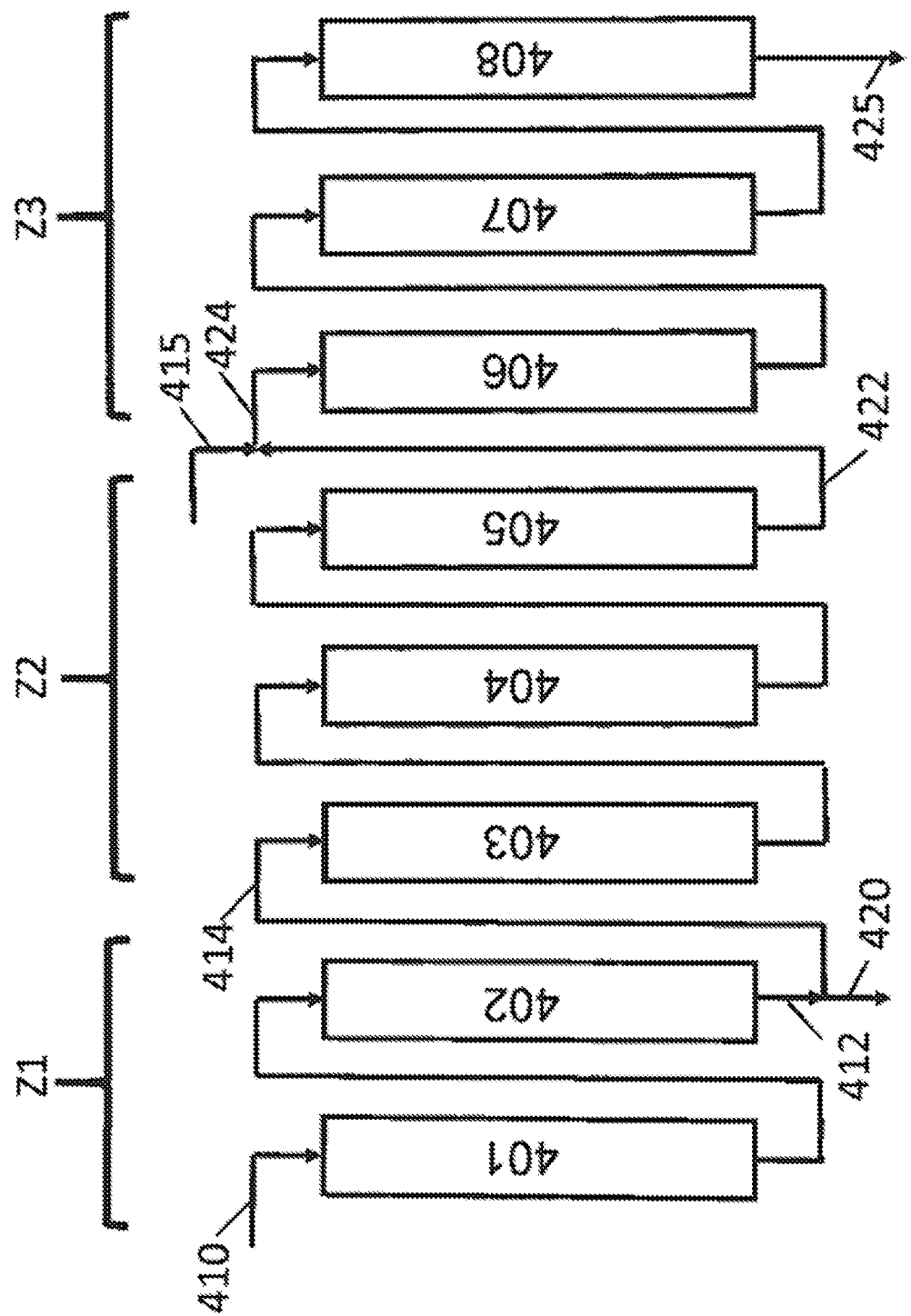
FIG. 8 is a schematic process flow diagram illustrating a configuration of the simulated moving bed cycle for a Polishing Bed system experiment which is described in Example 3.

The polishing bed zone consisted of a plurality of adsorbent beds connected in series as shown in FIG. 8. The lab scale SMB unit, OCTAVE-300 (Available from Semba Biosciences, Inc., Madison, Wis.) was employed to operate the configuration shown in FIG. 8 as a continuous simulated moving bed system. With reference to FIG. 8, adsorbent beds 401, 402, 403, 404, 405, 406, 407, and 408 were disposed in serial fluid communication such that fluid introduced at the top of any adsorbent bed n continued to the next highest adsorbent bed n+1 by passing the effluent from adsorbent bed n from the bottom of adsorbent bed n to the top of the adjacent adsorbent bed n+1. The adsorbent beds were operated in three zones, zone 1 (Z1), zone 2 (Z2), and zone 3 (Z3), whereby the elute stream from the second swing bed was loaded on to zone 3 (Z3) by introducing the second swing bed elute via lines 415 and 424 to adsorbent bed 406. In zone 3 (Z3), steviol glycosides were adsorbed in adsorbent beds 406, 407 and 408, and a polishing bed raffinate steam was withdrawn in line 425 from adsorbent bed 408. In the same step, mobile phase desorbent, comprising DI water, was introduced in line 410 to zone 1 (Z1) and adsorbent bed 401, passing serially through adsorbent beds 401 and 402, and a polishing bed extract stream was withdrawn from adsorbent bed 402 via lines 412 and 420. A portion of the polishing bed extract stream in line 414 was passed to zone 2 (Z2) and introduced to the top of adsorbent bed 403, and continuing serially through adsorbent beds 403, 404 and 405. The effluent withdrawn from the bottom of adsorbent bed 405 was passed to the top of adsorbent bed 406 in line 422, and admixed with the second swing bed elute stream in line 415 before being passed to adsorbent bed 406 in line 424. In example 3, eight adsorbent bed columns constructed of polypropylene, each having an inside diameter of 2 inches and a length of 24 inches were packed with RESINDION PH-400 resin, a rigid low swelling phenylated polymethacrylate polymer adsorbent characterized by a highly porous structure with an particle size of 75-200 μm (Available from Mitsubishi Chemical Company, Tokyo, Japan). The eight adsorbent beds were arranged as shown in FIG. 8 and disposed in a water bath having a polishing bed temperature range of 55-70° C., averaging about 60° C. In each step of the simulated moving bed polishing bed cycle, the second swing bed elute, having a concentration of 25 g/l in water was loaded in zone 3 (Z3) as discussed hereinabove. During each step, only one column in zone 3 (Z3) received the feed. In zone 3 (Z3), at least a portion of the fatty acid and sugar impurities, such as phospholipids and saccharides, in the second swing bed elute were removed as a primary raffinate stream (line 425). The polishing bed primary raffinate stream is essentially a waste stream, and was continuously sent to waste disposal. Zone 2 (Z2) is a separation zone and in zone 2 the separation of steviol glycosides from the fatty acid and sugar impurities takes place. The desorbent (water) was loaded on to the adsorbent beds 401 and 402 in Zone 1 in series and a polishing bed extract stream was withdrawn in lines 412 and 420. The eight adsorbent beds were operated as a simulated moving bed system. Table 3 shows the SMB operating parameters for the operation of the second swing bed simulated moving bed zone.

TABLE 3

SMB Operating Parameters- Second Swing Bed SMB

| PARAMETER | VALUE | UNITS |
|---|---|---|
| Step Time | 10 | Minutes |
| Bath Temperature | 60 | ° C. |
| Feed Rate (SB2 Elute) | 25.0 | ml/minute |
| Desorbent (DI Water) | 170 | ml/minute |
| Polishing Bed Extract | 64 | ml/minute |
| Polishing Bed Raffinate | 131 | ml/minute |

The polishing bed extract stream had a total steviol glycoside purity of 97 wt. % on an anhydrous basis, and the recovery of the polishing bed extract represented a total steviol glycoside recovery of 75% on a weight basis, relative to the feed to the polishing bed simulated moving bed zone. Thus, the purity of the second swing bed (SB2) elute was enhanced from a concentration of 85 wt. % of sweet steviol glycosides (Rebaudioside A (A), Stevioside(S), and Rebaudioside C(C)) on an anhydrous basis, to an enhanced concentration of 97 wt. % sweet steviol glycosides (Rebaudioside A (A), Stevioside(S), and Rebaudioside C(C)) on an anhydrous basis.

Figure 9:
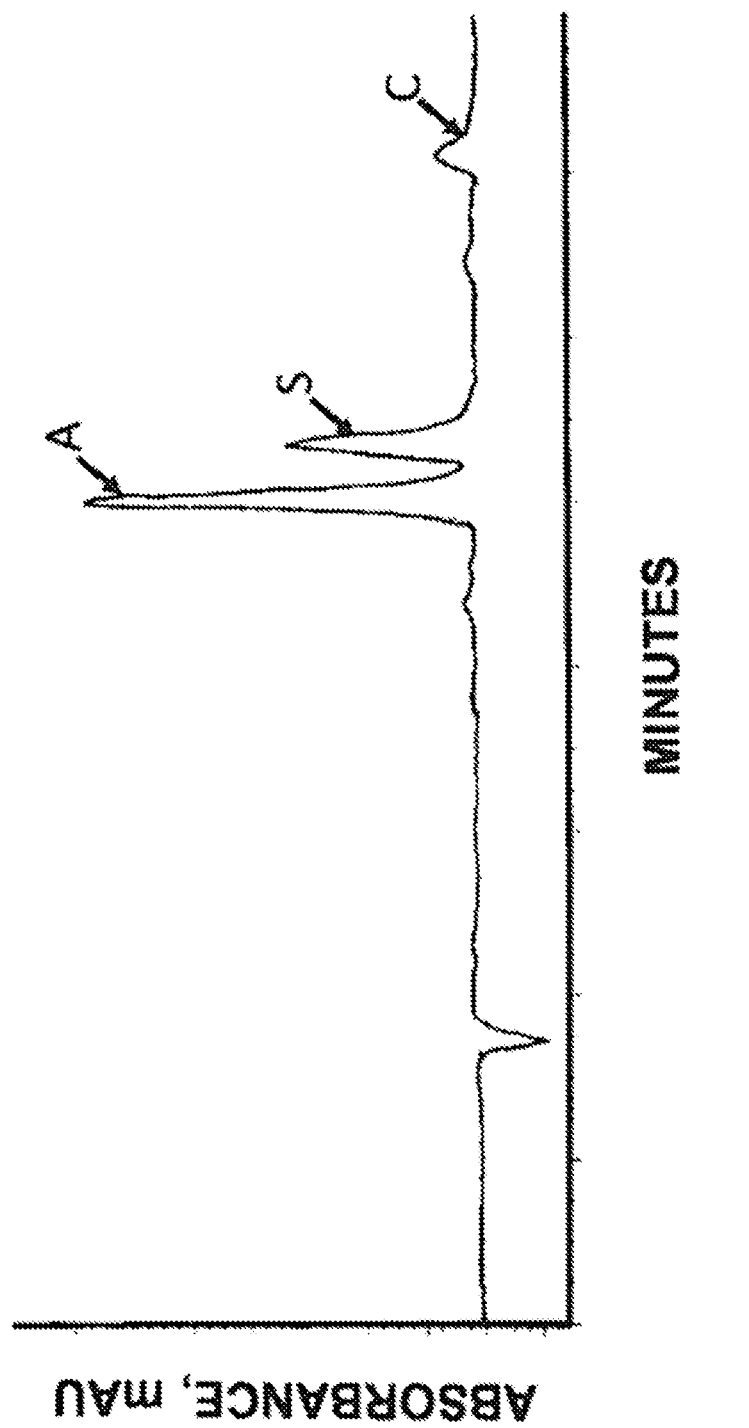
FIG. 9 is a High Performance Liquid Chromatography (HPLC) chromatographic area plot showing the results of a composition analysis of the polishing bed extract stream withdrawn from the polishing bed simulated moving bed zone of the present invention.

FIG. 9 is a High Performance Liquid Chromatography (HPLC) chromatographic area plot showing the results of a composition analysis of the polishing bed extract stream withdrawn from the polishing bed simulated moving bed zone of the present invention showing that the polishing bed extract stream essentially consists of sweet steviol glycosides: Rebaudioside A, Stevioside, and Rebaudioside C.

Example 4—Polishing Bed Simulated Moving Bed Zone

Using the same lab scale SMB unit, OCTAVE-300 (Available from Semba Biosciences, Inc., Madison, Wis.) of Example 3, the same process configuration shown in FIG. 8 was operated as a continuous simulated moving bed system as described in Example 3 for a feed which comprised 95 wt. % total steviol glycosides on an anhydrous basis. The eight adsorbent beds were operated as a simulated moving bed system Table 4 shows the SMB operating parameters for the operation of the polishing bed simulated moving bed zone.

TABLE 4

SMB Operating Parameters - Polishing Bed SMB

| PARAMETER | VALUE | UNITS |
|---|---|---|
| Step Time | 6 | Minutes |
| Bath Temperature | 60 | ° C. |
| Feed Rate (Elute) | 1.0 | ml/minute |
| Desorbent (DI Water) | 25 | ml/minute |
| Polishing Bed Extract | 4.7 | ml/minute |
| Polishing Bed Raffinate | 21.3 | ml/minute |

Figure 10:
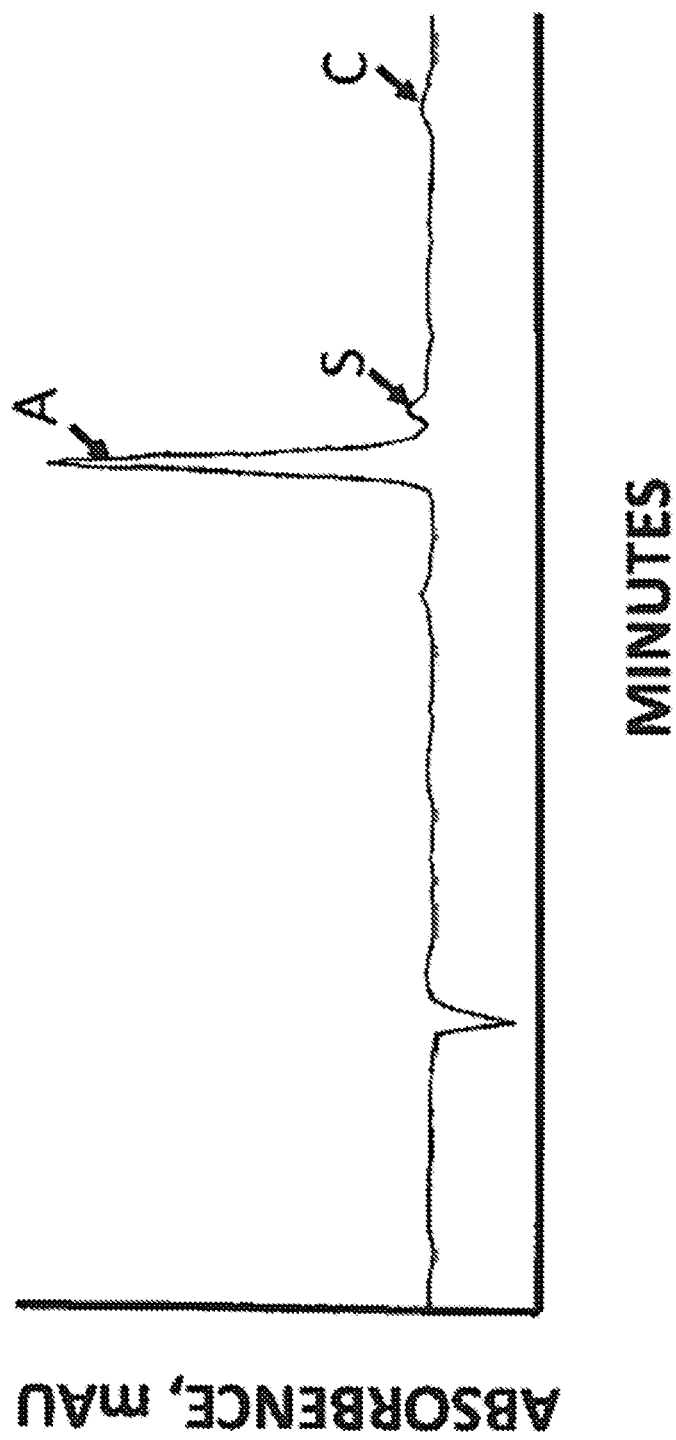
FIG. 10 is a High Performance Liquid Chromatography (HPLC) chromatographic area plot showing the results of a composition analysis of an enriched polishing bed extract stream of the present invention.

The resulting polishing bed extract of Example 4 showed enrichment of the feed to provide a polishing bed extract stream having a total steviol glycoside purity of 98 wt. % on an anhydrous basis, and having a ratio of Rebaudioside A (A), to Stevioside (S) ranging from 2.4 to 2.5 (w/w, %) (See FIG. 10).

FIG. 10 is a High Performance Liquid Chromatography (HPLC) chromatographic area plot showing the results of a composition analysis of the enriched polishing bed extract stream having a sweet steviol glycoside concentration of 98 wt. % on an anhydrous basis.

Example 5—Overall Process Improvement of Composition

A steviol extract prepared from the extraction of stevia leaves using conventional hot water extraction was subjected to the continuous process of the present invention according to the process flow as shown in FIG. 1 and the operating conditions discussed hereinabove. Table 5 presents the composition of the terminal product streams of the simulated moving bed zones of the present invention and shows how the steviol glycoside purity was increased in each process step from the initial steviol glycoside purity of about 40.5% (w/w) to a final polishing bed extract purity having a sweet steviol glycoside (Rebaudioside A (A), Stevioside(S), and Rebaudioside C(C)) concentration of greater than 95 wt. % (w/w).

TABLE 5

Steviol Glycoside Composition of SMB Zone Products

| Process Stream | Rebaudioside A, % (w/w) | Stevioside % (w/w) | Rebaudioside C % (w/w) | Total % (w/w) |
|---|---|---|---|---|
| Steviol Glycoside Extract | 28.25 | 9.25 | 3.0 | 40.50 |
| First Swing Bed Extract | 43.50 | 15.14 | 5.72 | 64.36 |
| Second Swing Bed Elute | 59.64 | 20.74 | 6.25 | 86.63 |
| Polishing Bed Extract | 62.56 | 26.09 | 6.62 | 95.27 |

Figure 11:
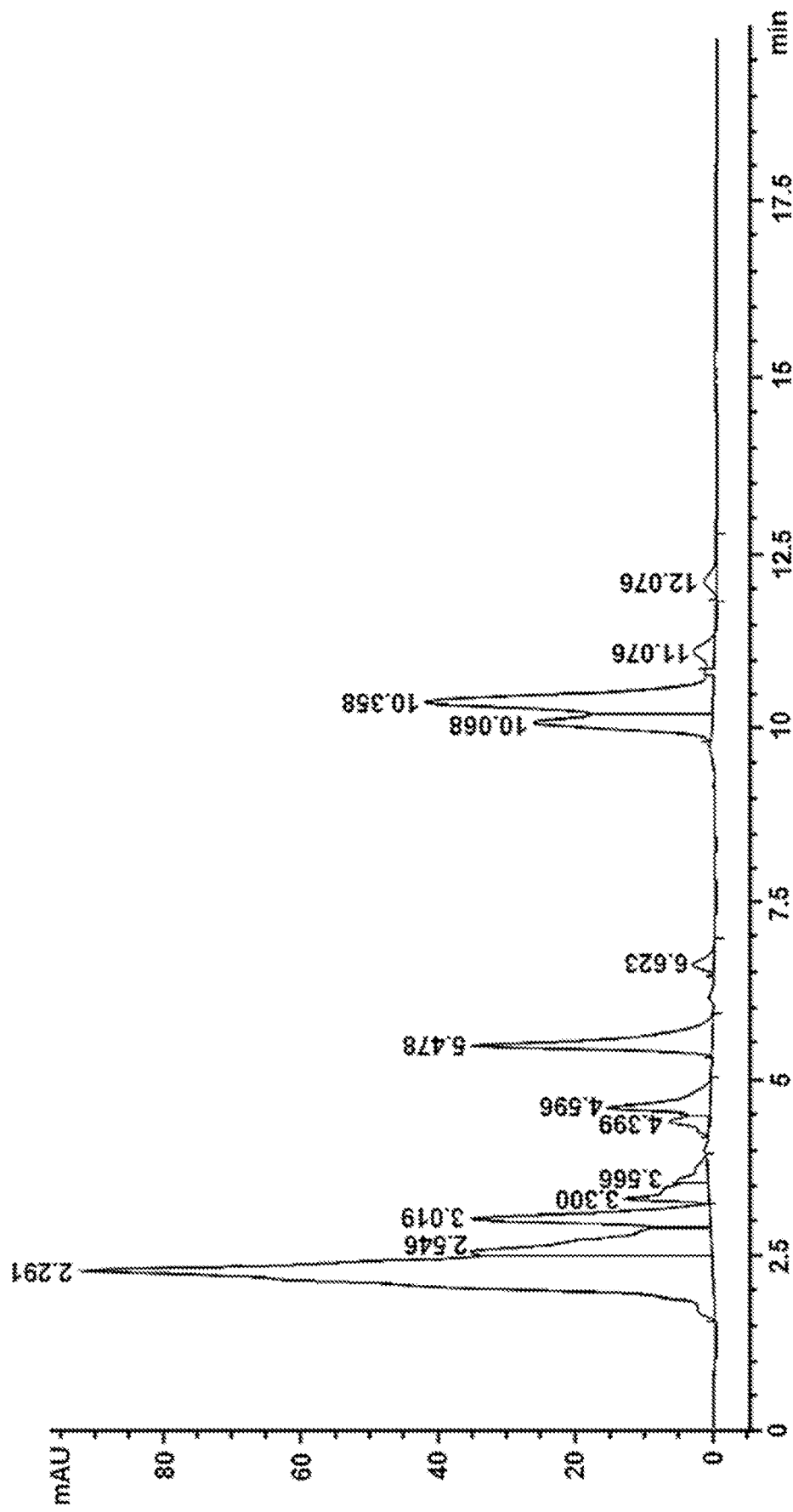
FIG. 11 is a High Performance Liquid Chromatography (HPLC) chromatographic area plot showing the analysis of a yeast fermentation broth.
Figure 12:
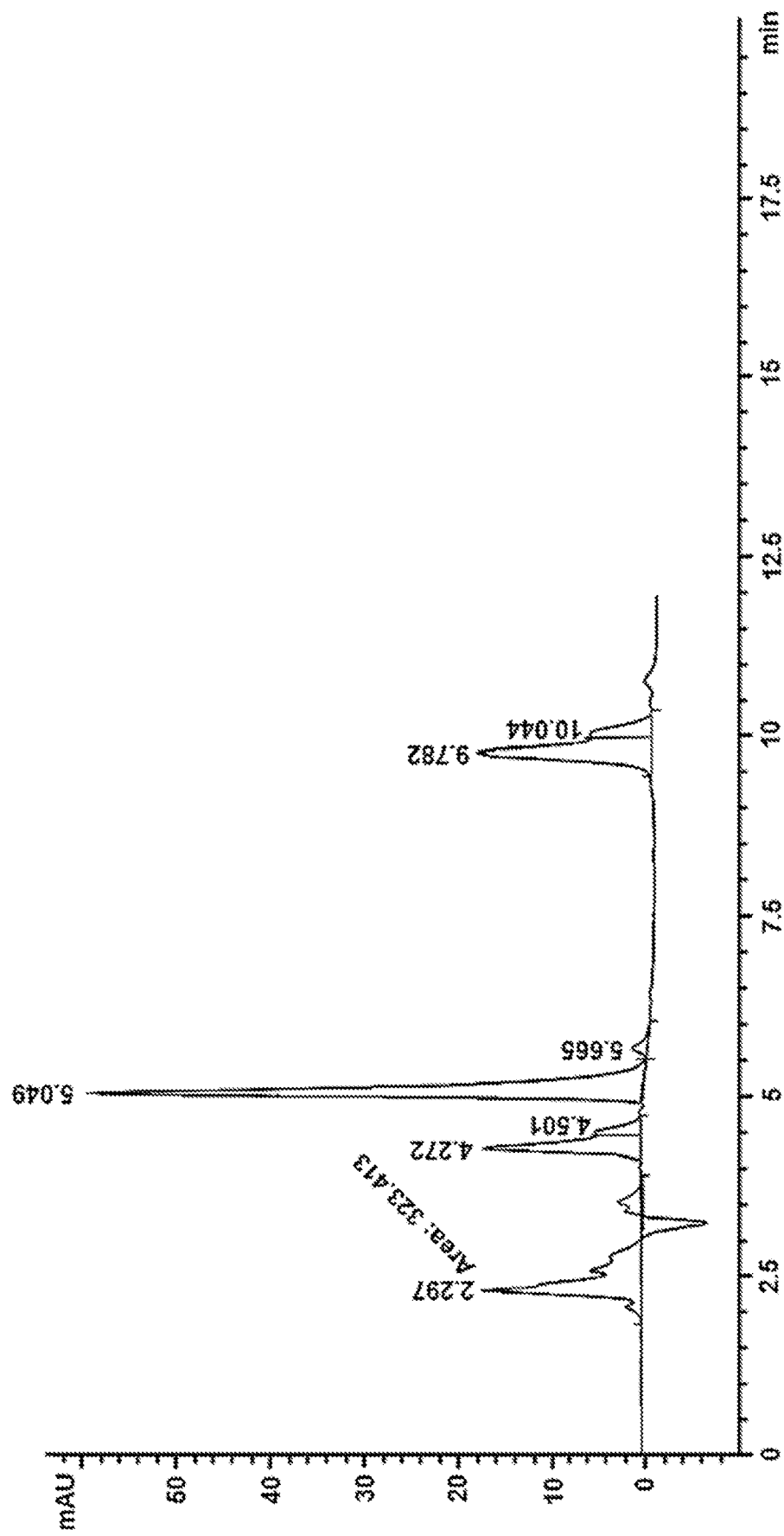
FIG. 12 is a High Performance Liquid Chromatography (HPLC) chromatographic area plot showing the results of a composition analysis of an enriched yeast fermentation broth using a hydrophobic interaction resin of the present invention.

Example 6—Purification of Rebaudioside D and Rebaudioside M from Yeast Fermentation Broth A 22×300 mm stainless steel column (114 mL) packed with hydrophobic interaction resin RELISORB PH400 (Available from Mitsubishi Chemical Company, Tokyo, Japan) was maintained at a temperature of 60° C. The resin was washed in sequential order with (1) two column volumes (CV) of 0.1 N NaOH at 5 mL/min, (2) two CVs of deionized water at 5 mL/min, (3) one CV of 0.1 N HCl at 5 mL/min, and (4) five CVs of deionized water at 5 mL/min to equilibrate at pH 5. Yeast fermentation broth (Available from Cargill, PF59A) was centrifuged and the resulting supernatant (20 mL at 20 mg/mL) was loaded on the column at 1.5 mL/min, and eluted with deionized water. The elution of steviol glycosides were monitored by high performance liquid chromatography using a C18 column. The pooled fractions were analyzed using HPLC with the following parameters:

Column: Orosil C18, 3 µm, 4.6×150 mm
Temperature: 40° C.
Mobile Phase: 69:31 10 mM Sod phosphate, pH 2.6, flow rate 0.6 ml/min The hydrophobic interaction resin removes the majority of front end impurities as demonstrated by the HPLC traces shown in FIGS. 11 and 12. FIG. 11. is an HPLC trace of the crude yeast fermentation broth and FIG. 12 is an HPLC trace after purification with the hydrophobic interaction resin. As demonstrated by FIGS. 11 and 12, the components residing from 2-4 minutes have been significantly reduced.

Example 7—Purification of Rebaudioside D and Rebaudioside M on Ion Exchange Resins A 10×250 mm stainless steel column (20 mL) packed with cationic resin DIAION PK216LH (Available from Mitsubishi Chemical Company, Tokyo, Japan) was washed in sequential order with (1) 1.5 column volumes (CV) of 0.2 N HCl at 1.5 mL/min and (2) 1.5 CVs of deionized water at 1.5 mL/min. A second 10×250 mm stainless steel column (20 mL) packed with anionic resin RELITE RAM2 (Available from Mitsubishi Chemical Company, Tokyo, Japan) was washed in sequential order with (1) 1.5 CVs of 0.5 N NaOH at 1.5 mL/min and (2) 1.5 CVs of deionized water at 1.5 mL/min. The two columns were connected in series and washed with 20 CVs of deionized water at 1 mL/min until the anionic column effluent had a pH of 7.2.

The purified fractions from Example 6 (18 mL) were loaded at 1 mL/min and eluted with deionized water. The elution of steviol glycosides were monitored by high performance liquid chromatography using a C18 column. The pooled fractions were analyzed using HPLC with the following parameters:

Column: Orosil C18, 3 µm, 4.6×150 mm
Temperature: 40° C.
Mobile Phase: 69:31 10 mM Sod phosphate, pH 2.6, flow rate 0.6 ml/min.

Figure 13:
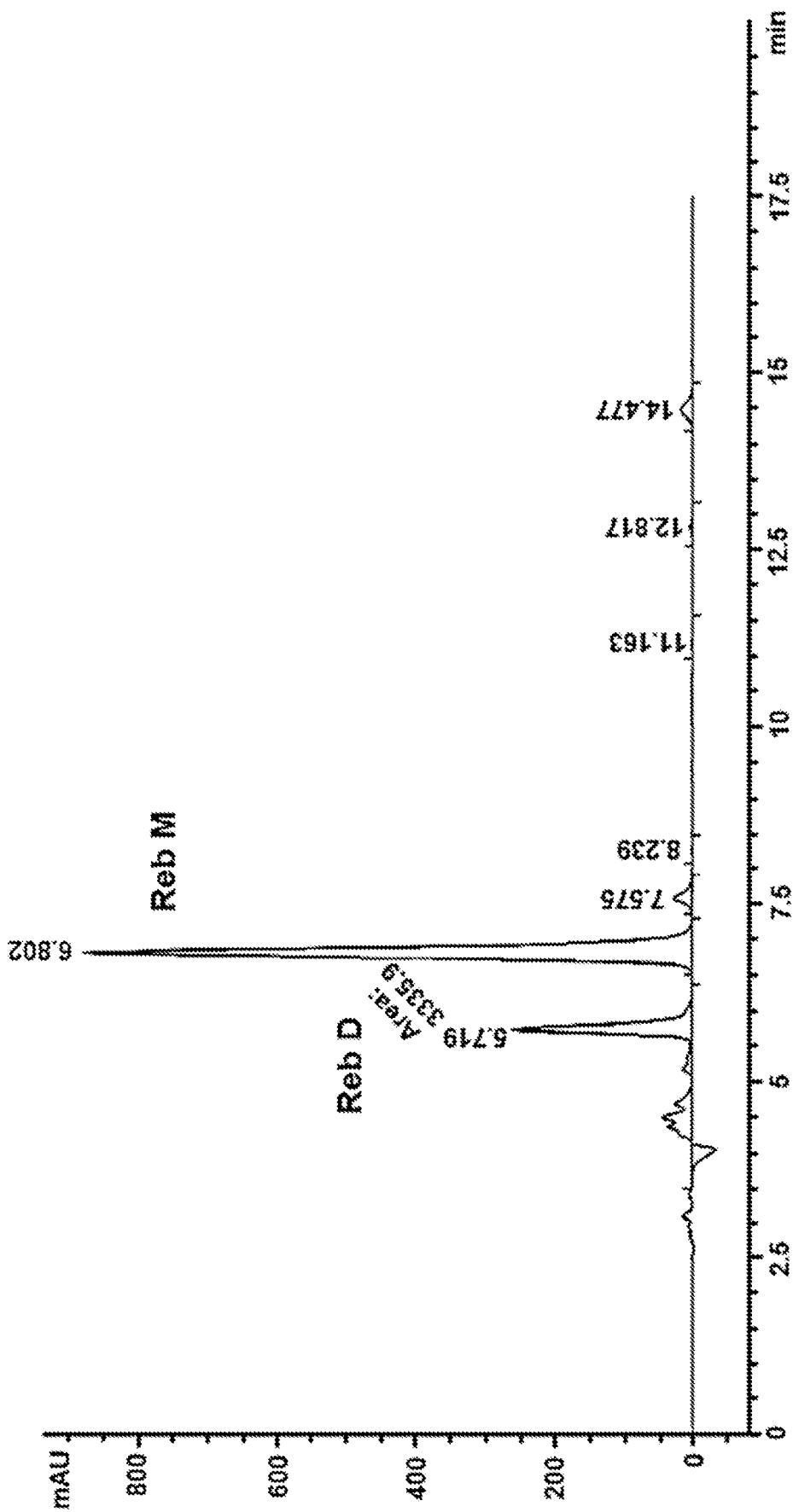
FIG. 13 is a High Performance Liquid Chromatography (HPLC) chromatographic area plot showing the results of a composition analysis of an enriched yeast fermentation broth using a hydrophobic interaction resin, a cationic resin, and an anionic resin of the present invention.

The combination of cationic and anionic resins removes the majority of impurities remaining after purification with the hydrophobic interaction resin, as demonstrated by FIG. 13. FIG. 13 is an HPLC trace of the pooled fraction containing Rebaudioside D and Rebaudioside M, as labeled in the HPLC trace at 5.7 minutes and 6.6 minutes.

The purity of the sample obtained after purification with the cationic and anionic resins was further assessed using the Joint FAO/WHO Expert Committee on Food Additives (JECFA) method for determining purity. The results are set forth in Table 6.

TABLE 6

Purification of Rebaudio sides D and Rebaudioside M

| Sample | Purity* (wt. %) | Rebaudioside A (wt. %) | Rebaudioside D (wt. %) | Rebaudioside M (wt. %) |
|---|---|---|---|---|
| Fermentation Broth | 22.5 | ND | 7.1 | 15.4 |
| Purified Sample | 95.0 | 1.4 | 17.5 | 76.0 |

*Purity was determined as described in JECFA method

As demonstrated by Table 6, the purity of Rebaudioside D and Rebaudioside M increases significantly from a purity of 22.5 wt. % to a purity of 95 wt. % upon purification with the combination of a hydrophobic interaction resin, cationic resin, and anionic resin.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. As used herein, the term "exemplary" indicates an example thereof and does not suggest a best or optimal of the recited item. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of purifying one or more steviol glycosides from a mixture, the mixture including the one or more steviol glycosides and at least one impurity, the method comprising:

passing the mixture through a first adsorbent with a first solvent, the first adsorbent arranged in an SMB configuration to form a first SMB zone, wherein passing the mixture through the first adsorbent with the first solvent comprises passing the mixture through the first SMB zone, the first adsorbent comprising one or more porous hydrophobic interaction resins having a particle size of 70-200 microns to provide a first eluate stream, the first eluate stream having the first solvent and a higher purity of the one or more steviol glycosides than in the mixture as measured by weight percentage of the solid content, and optionally removing at least a portion of the first solvent from the first eluate stream to provide a reduced first eluate stream.

2. The method of claim 1, the method further comprising:

passing the first eluate stream or the reduced first eluate stream through a second adsorbent with a second solvent, the second adsorbent comprising one or more hydrophobic interaction resins or one or more ion exchange resins to provide a second eluate stream, the second eluate stream having the second solvent and a higher purity of the one or more steviol glycosides than in the first eluate stream or the reduced first eluate stream as measured by weight percentage of the solid content, and optionally removing at least a portion of the second solvent from the second eluate stream to provide a reduced second eluate stream.

3. The method of claim 1, wherein the one or more steviol glycosides are selected from the group consisting of Dulcoside A, Rebaudioside C, Rebaudioside A, Stevioside, Rebaudioside B, Rebaudioside D, Rebaudioside E, Rebaudioside F, Rebaudioside M, Rebaudioside I, Steviolbioside, and Rubusoside.

4. The method of claim 1, wherein the one or more steviol glycosides are Rebaudioside D and Rebaudioside M.

5. The method of claim 1, wherein the one or more steviol glycosides is Rebaudioside D.

6. The method of claim 1, wherein the one or more steviol glycosides is Rebaudioside M.

7. The method of claim 1, wherein the mixture is a stevia plant extract, a stevia fermentation broth, a yeast fermentation broth, an *Escherichia coli* fermentation broth, or an enzyme-converted mixture.

8. The method of claim 7, wherein the stevia plant is *Stevia rebaudiana Bertoni*.

9. The method of claim 2, wherein the first solvent and the second solvent comprise water.

10. The method of claim 9, wherein the first solvent and the second solvent comprise greater than 95% v/v water.

11. The method of claim 10, wherein the first solvent and the second solvent comprise greater than 99% v/v water.

12. The method of claim 11, wherein the first solvent and the second solvent are water.

13. The method of claim 1, wherein said at least one impurity comprises at least one of tri-terpenes, sterols, flavonoids, volatile oils, pigments, gums, proteins, carotenoids, chlorophyll, vitamins, phospholipids, saccharides, solid insoluble, salts, fermentation byproducts, or N-acetyl glucosamine.

14. The method of claim 4, wherein said at least one impurity comprises a second steviol glycoside selected from Dulcoside A, Rebaudioside C, Rebaudioside A, Stevioside, Rebaudioside B, Rebaudioside E, Rebaudioside F, Rebaudioside I, Steviolbioside, Rubusoside, and combinations thereof.

15. The method of claim 2, wherein the second adsorbent is one or more ion exchange resins.

16. The method of claim 15, wherein the one or more ion exchange resins is a combination of a cationic resin and an anionic resin.

17. The method of claim 16, wherein the cationic resin and anionic resin are arranged in series.

18. The method of claim 16, wherein the cationic resin is a styrene-divinylbenzene copolymer resin and the anionic resin is an acrylic-divinylbenzene copolymer resin.

19. The method of claim 2, wherein the second adsorbent is arranged in a SMB configuration to form a second SMB zone, and wherein passing the first eluate stream or the reduced first eluate stream through the second adsorbent with the second solvent comprises passing the first eluate stream or the reduced first eluate stream through the second SMB zone.

20. The method of claim 1, the method further comprising:

preconditioning the first adsorbent prior to passing the mixture through a first adsorbent with a first solvent.

21. The method of claim 20, wherein preconditioning comprises washing with acid, base, water, or a combination thereof.

22. The method of claim 2, the method further comprising:
- preconditioning the first adsorbent prior to passing the mixture through a first adsorbent with a first solvent;
- preconditioning the second adsorbent prior to passing the first eluate stream or the reduced first eluate stream through a second adsorbent with a second solvent.

23. The method of claim 22, wherein preconditioning comprises washing with acid, base, water, or a combination thereof.

24. The method of claim 2, the method further comprising:
- drying the second eluate stream or the reduced second eluate stream.

* * * * *